United States Patent
McLaughlin et al.

(10) Patent No.: US 11,027,122 B2
(45) Date of Patent: Jun. 8, 2021

(54) SPINAL CORD STIMULATION METHOD TO TREAT LATERAL NEURAL TISSUES

(71) Applicant: Micro-Leads, Inc., Boston, MA (US)

(72) Inventors: Bryan L. McLaughlin, Cambridge, MA (US); Kevin Meador, Boston, MA (US); Girish Chitnis, Watertown, MA (US); John Ogren, Antrim, NH (US)

(73) Assignee: Micro-Leads, Inc., Somerville, MA (US)

( * ) Notice: Subject to any disclaimer, the term of this patent is extended or adjusted under 35 U.S.C. 154(b) by 245 days.

(21) Appl. No.: 15/876,035

(22) Filed: Jan. 19, 2018

(65) Prior Publication Data

US 2018/0200505 A1 Jul. 19, 2018

Related U.S. Application Data

(60) Provisional application No. 62/447,961, filed on Jan. 19, 2017.

(51) Int. Cl.
*A61N 1/05* (2006.01)
*A61N 1/36* (2006.01)

(52) U.S. Cl.
CPC ........ *A61N 1/0551* (2013.01); *A61N 1/36062* (2017.08); *A61N 1/36071* (2013.01)

(58) Field of Classification Search
CPC .............. A61N 1/0551; A61N 1/36062; A61N 1/36071
See application file for complete search history.

(56) References Cited

U.S. PATENT DOCUMENTS

| | | | |
|---|---|---|---|
| 4,941,961 A | 7/1990 | Noguchi et al. |
| 5,417,719 A | 5/1995 | Hull et al. |
| 6,024,702 A | 2/2000 | Iversen |
| 6,871,099 B1 | 3/2005 | Whitehurst et al. |
| 7,613,524 B2 | 11/2009 | Jordan |
| 7,697,995 B2 | 4/2010 | Cross, Jr. et al. |
| 8,805,542 B2 | 8/2014 | Tai et al. |
| 9,095,699 B2 | 8/2015 | Rosenberg et al. |
| 9,174,038 B2 | 11/2015 | Schüttler et al. |

(Continued)

FOREIGN PATENT DOCUMENTS

WO WO 2007/039735 A1 4/2007

OTHER PUBLICATIONS

Schuettler et al., *Fabrication of implantable microelectrode arrays by laser cutting of silicone rubber and platinum foil*, http://iopscience.iop.org/article/10.1088/1741-2560/2/1/013/pdf, Journal of Neural Engineering, Institute of Physics Publishing, vol. 2, No. 1, Feb. 22, 2005, pp. S121-S128.

(Continued)

*Primary Examiner* — Joseph M Dietrich
(74) *Attorney, Agent, or Firm* — Nutter McClennen & Fish LLP

(57) ABSTRACT

A method assists a person by providing an electrode array having a substrate supporting a plurality of stimulation contacts configured to stimulate at least a portion of the spinal cord neural tissue. The method also implants, in a medically uncompressed manner, the therapy array in the epidural space, where a portion of the therapy array is positioned adjacent to at least one pedicle with stimulation contacts positioned adjacent to at least one dorsal root laterally and at least one fasciculi of the dorsal column within the vertebral foramen at one or more vertebral levels.

35 Claims, 29 Drawing Sheets

(56) References Cited

U.S. PATENT DOCUMENTS

| | | |
|---|---|---|
| 9,364,660 B2 | 6/2016 | Howard et al. |
| 9,387,326 B2 | 7/2016 | Moffitt |
| 9,409,023 B2 | 8/2016 | Burdick et al. |
| 9,561,363 B2 | 2/2017 | Skubitz et al. |
| 9,572,976 B2 | 2/2017 | Howard et al. |
| 9,656,085 B2 | 5/2017 | Moffitt et al. |
| 2006/0257672 A1 | 11/2006 | Horikoshi et al. |
| 2011/0270350 A1 | 11/2011 | Feler et al. |
| 2012/0006793 A1 | 1/2012 | Swanson |
| 2012/0245449 A1 | 9/2012 | Williams et al. |
| 2013/0060313 A1 | 3/2013 | Cross, Jr. |
| 2013/0345780 A1 | 12/2013 | Tabada et al. |
| 2014/0128954 A1 | 5/2014 | Schüttler et al. |
| 2014/0180361 A1 | 6/2014 | Burdick et al. |
| 2014/0180370 A1 | 6/2014 | Romero |
| 2016/0213917 A1 | 7/2016 | Dalm et al. |
| 2017/0120056 A1 | 5/2017 | Woods et al. |
| 2017/0157390 A1 | 6/2017 | Howard et al. |
| 2017/0246452 A1 | 8/2017 | Liu et al. |

OTHER PUBLICATIONS

Schuettler et al., *Stretchable Tracks for Laser-Machined Neural Electrode Arrays*, 31$^{st}$ Annual International Conference of the IEEE EMBS, Minneapolis, MN, USA, Sep. 2-6, 2009, pp. 1612-1615.
International Searching Authority, Application No. PCT/US18/14566 dated Mar. 29, 2018, together with the Written Opinion of the International Searching Authority, 13 pages.

SPINAL CORD STIMULATION METHOD TO TREAT LATERAL NEURAL TISSUES

PRIORITY

This patent application claims priority from provisional U.S. patent application No. 62/447,961, filed Jan. 19, 2017, entitled, "METHOD OF SPINAL CORD STIMULATION TO TREAT CHRONIC PAIN ASSOCIATED WITH LATERAL FIBERS," and naming Bryan McLaughlin and Kevin Meador as inventors, the disclosure of which is incorporated herein, in its entirety, by reference.

GOVERNMENTAL SUPPORT

This invention was made with government support under W911NF-15-C-0007 awarded by US ARMY Contracting Command-Aberdeen (ACC-APG-RTP W911NF). The government has certain rights in the invention.

FIELD OF THE INVENTION

The invention generally relates to neurostimulation devices and methods and, more particularly, the invention relates to neurostimulation devices and methods for effectively managing sensory information passing through lateral fibers and dorsal roots of the posterior dorsal column of the spinal cord.

BACKGROUND OF THE INVENTION

While implantable medical devices for spinal cord stimulation effectively treat chronic neuropathic pain of the extremities, successfully and predictably targeting laterally positioned dorsal column fibers and nerve roots to relieve pain associated with those dermatomes (e.g., trunk pain, axial low-back, etc) has been an ongoing challenge. In particular, if a patient feels pain in a dermatome, and the sensory nerve fibers associated with that dermatome are positioned laterally within the dorsal column or in the dorsal roots, consistently providing pain therapy can be problematic. The lateral location of these nerve fibers and roots combined with the poor proximity of conventional electrode contacts with respect to those fibers has resulted in limited pain reduction and poor patient outcomes.

The spinal cord posterior dorsal column has vertically ascending columns and nerve roots extending horizontally. Conventional electrodes can successfully target the medial fibers of the dorsal column. Undesirably, however, conventional electrodes often are thick and bulky, which limits their ability to be positioned relatively significant distances from the anatomical midline. Consequently, the total electrode span and flatness associated with a thick plate-type geometry has limited the proximity and coupling efficiency, making controlled electrical stimulation of lateral fibers and nerve roots extremely difficult. Other indications, such as lower urinary tract function, chronic headaches, and motor function may also be treatable by stimulating lateral fibers and dorsal roots.

SUMMARY OF VARIOUS EMBODIMENTS

In accordance with one embodiment of the invention, a method assists a person having expected human anatomy. Among other things, the person has spinal cord neural tissue, a plurality of ascending dorsal column fibers, neural tissue protected by dura mater and cerebrospinal fluid, and dorsal roots. The person also has at least two pedicles and a vertebral foramen. The method assists the person by providing a flexible electrode array having a substrate supporting a plurality of stimulation contacts configured to stimulate at least a portion of the spinal cord neural tissue and/or dorsal root(s). At least one of the plurality of stimulation contacts is/are configured to be independently stimulated relative to the other contacts.

The method implants the flexible therapy array (aka "electrode array") in the epidural space where a first portion of the array is positioned adjacent to at least one pedicle and/or at least one dorsal root laterally within the vertebral foramen and longitudinally spans one or more vertebral levels. As such, at least one stimulation contact is adjacent to at least one dorsal root. The substrate of the flexible therapy array is configured to be conformable to the dura mater after implanting. In addition, the substrate has a first region, with stimulation a contact, having a first thickness and flexibility that enables implantation adjacent to the at least one pedicle in a medically uncompressed manner relative to at least one dorsal root, and a second region with a stimulation contact and a second thickness that enables the substrate to be positioned medially (at least in part). The first thickness is less than or equal to the second thickness. The uncompressed implantation is configured not to compress the dura mater and/or cerebrospinal fluid more than 1.2 mm after implantation to mitigate abnormal and therapy reducing root activation thresholds.

The vertebral foramen comprises a normal vertebral foramen—i.e., without the vertebral foramen surgically altered to receive the therapy array. In other words, the vertebral foramen in its substantially natural state.

Some embodiments implant the flexible array adjacent to at least one of the dorsal column fibers (e.g., adjacent to a first fasciculus of a plurality of fasciculi). Alternatively or in addition, the method may implant the flexible array adjacent to at least one of the dorsal root entry zones. After the therapy array is inserted, the method may actuate the therapy array to stimulate at least one portion of the dorsal column fibers and/or the dorsal root. For example, the method may actuate the therapy array to stimulate the first fasciculus without stimulating the first dorsal root, stimulate the dorsal root without stimulating the first fasciculus, or stimulate the first fasciculus and the first dorsal root at the same time.

The substrate preferably is formed from one or more flexible materials, such as silicone, to enable conformity to the dura mater. Accordingly, the therapy array may be implanted in the epidural space both medially and laterally. For example, the flexible therapy array may have a lateral span from the left pedicle to the right pedicle. The plurality of stimulation contacts may form an array of stimulation contacts having at least four rows and at least four columns, and no more than 20 rows and 20 columns. To fit in the various lateral and medial regions of the epidural region, the first region of the substrate, the first region may be between about 0.75 mm and about 1.25 mm, further wherein the second region of the substrate may be between about 0.75 mm and about 1.25 mm. For further functionality, the substrate also may be configured to be folded on at least two intersecting planes.

In accordance with another embodiment, a method assists a person (with the noted anatomy and other unnoted anatomy) by providing a flexible therapy array having a substrate supporting a plurality of stimulation contacts configured to stimulate spinal cord neural tissue. At least one of the plurality of stimulation contacts is configured to be independently stimulated relative to the other stimulation contacts. The substrate is configured to be flexible and has a prescribed thickness of between 0.1 mm and 1.2 mm. The method implants the flexible therapy array (e.g., one edge of the array) adjacent to the pedicle in the epidural space with stimulation contacts adjacent to one or both of the dorsal column and the dorsal root entry zone of a first dorsal root. The flexible therapy array also is within the normal vertebral foramen at one or more vertebral levels. The substrate of the flexible therapy array is configured to be conformable to the dura mater after implantation. Moreover, the substrate has one or more regions that each have prescribed (often different) thicknesses and/or stiffnesses to implant within the epidural space, adjacent to the pedicle.

In accordance with other embodiments, a method assists a person (with the noted anatomy and other unnoted anatomy) by providing an electrode array having a substrate supporting a plurality of stimulation contacts configured to stimulate at least a portion of the spinal cord neural tissue. The method also implants, in a medically uncompressed manner, the therapy array adjacent to the pedicle in the epidural space, where a portion of the therapy array is positioned adjacent to at least one pedicle and/or at least one dorsal root laterally within the vertebral foramen at one or more vertebral levels.

It should be noted that although not necessarily discussed as such above, various features and portions of the method discussed in this Summary section may be combined together in various embodiments.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

Figure 1:
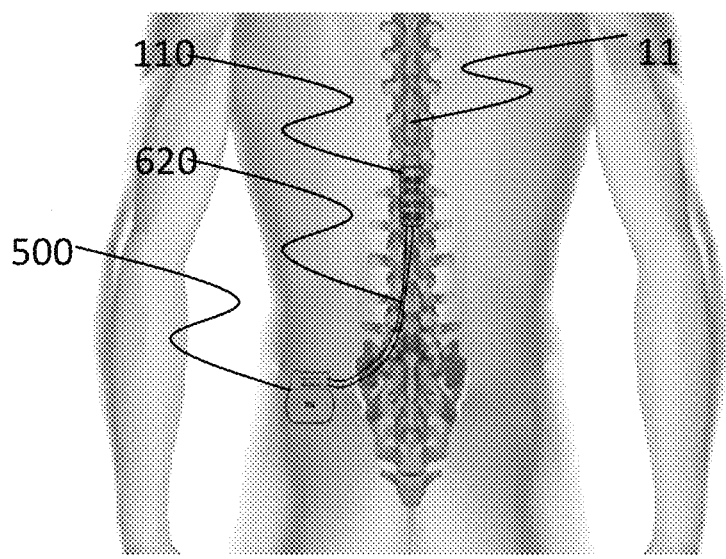
FIG. 1 schematically shows a person's/patient's body and the position of the spine with one embodiment of a therapy array in a typical implantation location and implanted generator ("IPG") connected to the electrode array.

Illustrative embodiments implant an electrode array in a person's epidural space in a medically uncompressed manner; namely, in a manner that does not compress the person's dura mater and/or cerebrospinal fluid relative to at least one dorsal root more than 1.2 mm after implantation. By implanting with this method, illustrative embodiments mitigate the likelihood of unsafe nerve compression injury or electrical hypersensitivity, assisting the person/patient. Details of illustrative embodiments are discussed below.

Neurostimulation of the spinal cord has successfully been used to treat acute and chronic pain occurring in the upper extremities, lower extremities, and trunk. Electrical energy imparted by the electrode array to the spinal cord and dorsal roots provides a perception of pain relief in one or more sub-regions of the patient's body. Multi-contact paddle electrode arrays with plate-type geometries provide more opportunities to treat pain as each contact (or therapy contact or therapy site) can deliver electrical stimuli to smaller tissue volumes adjacent to the contact.

Existing prior-art stimulation electrode arrays known to the inventors have had a limited surgical and therapeutic efficacy for treating various conditions, such as torso and lower back pain, trunk pain, foot pain, headaches, and bladder function. In the case of chronic pain, the standard-of-care implantation site for an electrode array is T9-T12, where nerve fibers associated with the lower back and torso are positioned at the lateral extent of the dorsal column or have not yet entered the dorsal column.

Prior-art paddle leads known to the inventors have inherent rigidity and bulk volumetric limitations that impede surgical positioning, and generally cannot be safely positioned adjacent to the nerve roots or the pedicle. Specifically, the cerebrospinal fluid volume and epidural thickness near the roots are very thin. At midline, the epidural space is maximal within the vertebral column but narrows and closes adjacent to the dorsal roots and pedicle. The cerebrospinal fluid thickness is the greatest medially (approximately 3-5 mm) and very thin laterally (less than 2 mm). While the placement of prior art paddle electrodes may be accommodated medially by flattening the dura mater, the lateral epidural space cannot accommodate such pressure or flattening of the dura mater without compression of the nerve roots and dorsal columns, causing significant surgical risk. In extreme cases, nerve root injury or paralysis may result from using such a prior-art electrode in these lateral regions.

To the inventors' knowledge, dorsal roots and dorsal root entry zones cannot be effectively controllably stimulated with prior art electrodes for two reasons: (1) safe implantation at the anatomical midline does not provide electrical contacts near the dorsal roots, lateral dorsal root entry zone, or lateral dorsal columns due to compression from electrode substrate volume, and (2) improper lateral medically compressed placement near the nerve roots typically leads to loss of therapy. Dorsal root stimulation may be independently applied and dorsal column stimulation may be independently applied to provide therapy to different sub-regions of the patient's body.

In a normal context, stimulation may be increasingly applied to the dorsal columns until a desired therapeutic benefit is derived in the patient. However, a crossover threshold amplitude is reached in which the dorsal root fibers become activated and the patient experiences discomfort (e.g., pain in the ribs). In a medically compressed context/manner, cerebrospinal fluid compression near the dorsal roots dramatically reduces the dorsal root threshold at which the patient experiences discomfort—i.e., compression undesirably causes the dorsal root to "fire" at significantly lower energy levels. Accordingly, when in such a medically compressed context/manner, stimulus amplitudes normally applied to the dorsal columns typically must be reduced to mitigate the compressed root discomfort, undesirably suppressing the therapeutic amplitude the patient may receive to the dorsal columns.

Recognizing this problem, the inventors developed a method of array implantation that mitigates such compression. To that end, various embodiments provide a therapeutic array with geometric and mechanical attributes that cause negligible or no medical compression and the consequent loss of therapy. In illustrative embodiments, the array has a plurality of stimulation contacts that each can be stimulated independently of, or collectively with, other of the contacts.

To enable greater efficacy of electrical stimulation, a medically non-compressed stimulation method implants an epidural paddle with electrodes adjacent to the dorsal roots and dorsal columns nearest the pedicle. As discussed above and below, the method implants the electrode array in a manner that does not cause a "medical compression" after implantation (i.e., a compression of spinal roots or dorsal columns that produces a noticeable discomfort in the patient).

Various embodiments provide pain relief in the patient, where the array substrate geometry and mechanical properties of the implanted system 100 do not compress the dorsal roots and other spinal column neural tissue. To illustrate this, FIG. 1 shows an implantable pulse generator ("IPG 500") connected to a therapy delivering array 110 near the spinal cord 14 over a lead body 620.

Patients with acute or chronic pain may experience total body pain, lumbar or axial back pain, radicular or segmental pain in the upper or lower extremities, and multi-focus pain from a variety of conditions. Those conditions may include failed back surgery syndrome (FBSS), complex regional pain syndrome (CRPS), or pain associated with shingles. Clinical trials have demonstrated that for many types of pain, 60% of patients have greater than 50% pain reduction after 6 months of stimulation therapy, which is greater than many alternative therapies. Illustrative embodiments relate primarily to spinal cord stimulation principally for the treatment of chronic pain, though other therapeutic benefits of spinal cord stimulation are envisioned.

Figure 3:
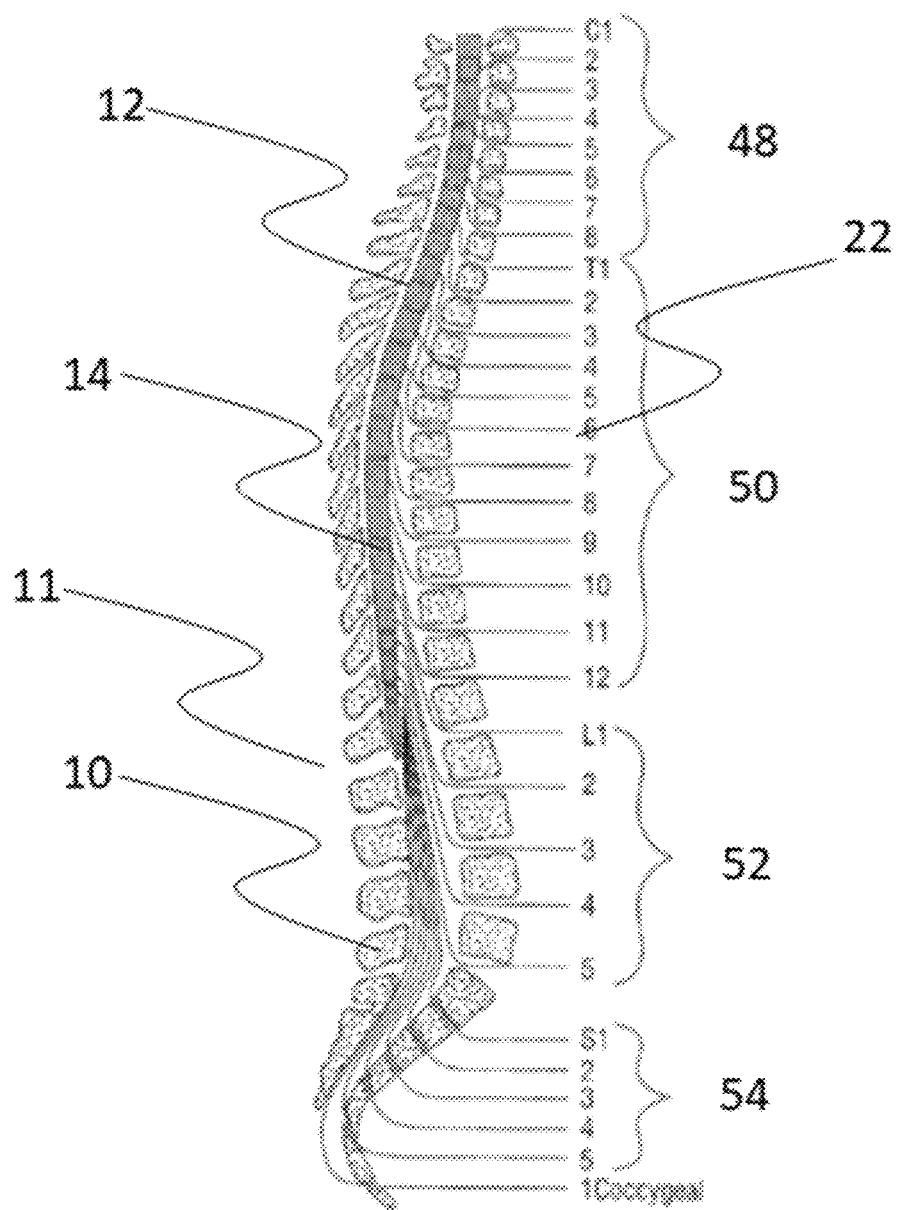
FIG. 3 schematically shows a sagittal cross section of the spinal column identifying the four vertebral regions and identifying the spinal nerves that exit the spine via the intervertebral foramen at each level.
Figure 4:
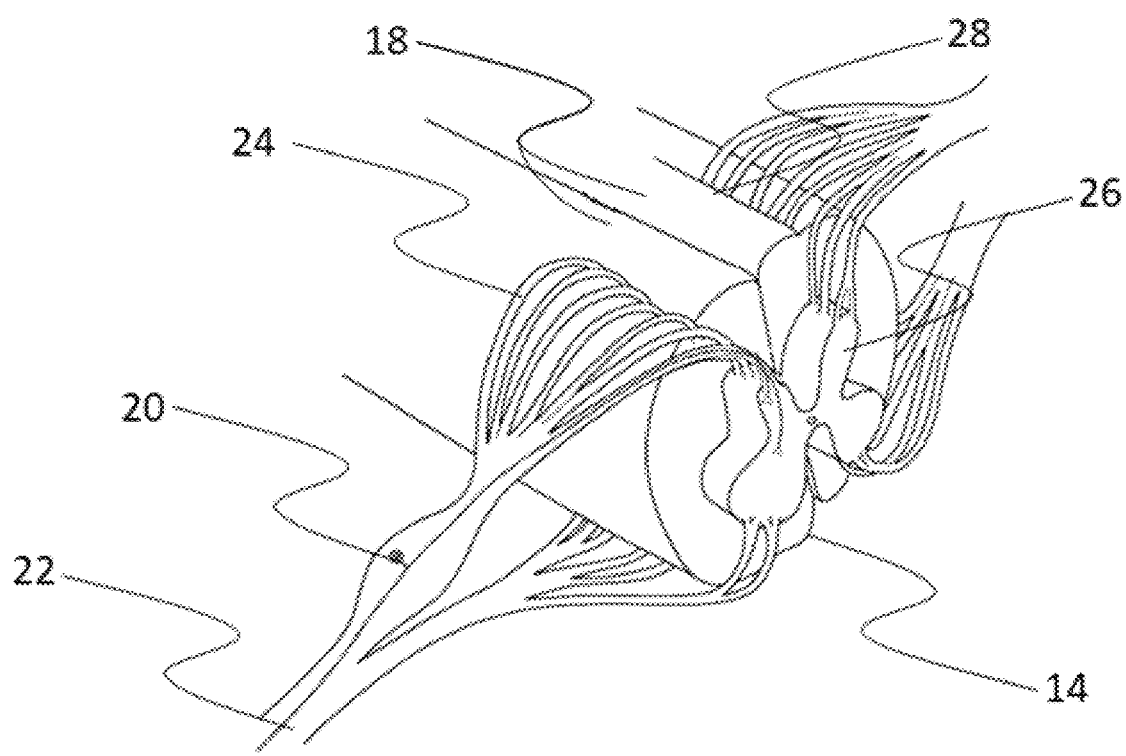
FIG. 4 diagrammatically shows the typical anatomy of the spinal cord with the spinal nerves, dorsal and ventral root branches and the dorsal root entry zone.
Figure 5:
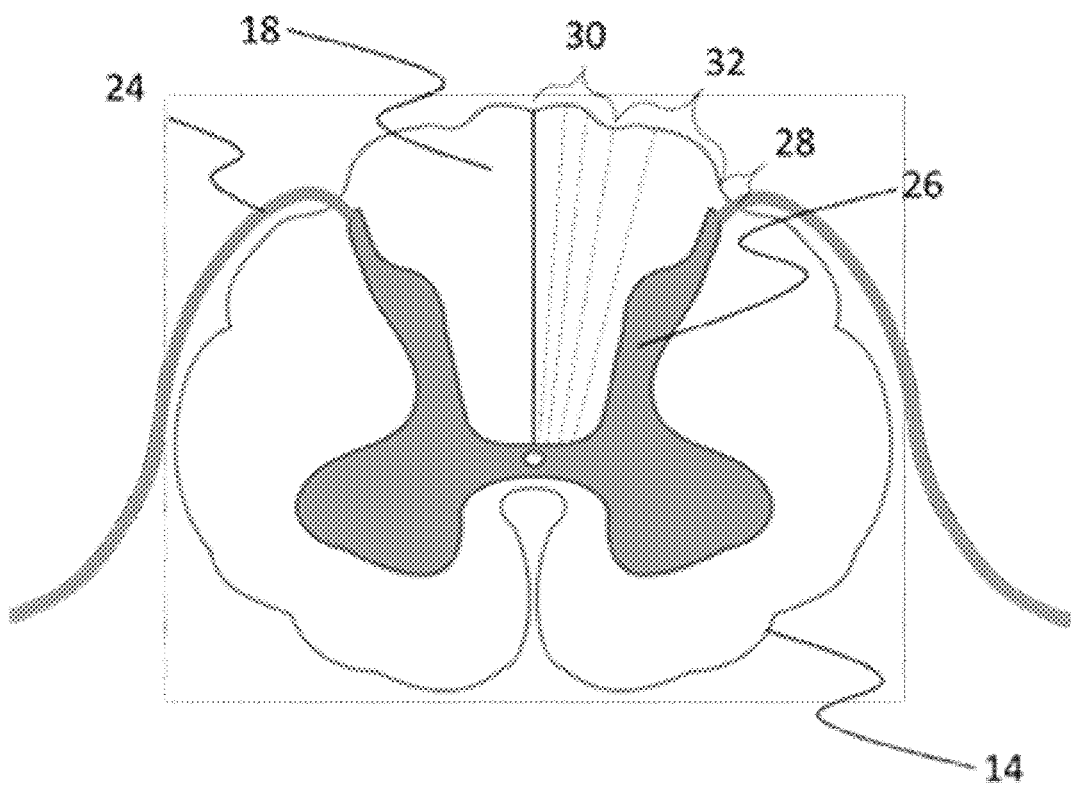
FIG. 5 schematically shows an anatomical cross-section of the spinal cord illustrating the dorsal horn, the dorsal roots, the dorsal column with fasciculi, and the dorsal root entry zone.

For example, with reference to FIGS. 3 and 4, stimulation of the dorsal root entry zone 28 and/or the dorsal roots 24 may treat abdominal or trunk pain at the thoracic level 50, or headaches or migraines at the cervical level 48. Illustrative embodiments also stimulate sacral S1-S4 54 nerve roots 24, which junction to form lower urinary tract (LUT) nerves that control bladder and urethral function. Stimulation at this region may enable the treatment for urinary tract dysfunction, overactive bladder, incontinence, or partial voiding syndromes. Other indications related to restoration of sensory perception, such as haptic feedback where extremities have suffered loss of sensation from neuropathies or amputation are also envisioned. Stimulation of the spinal reflex arcs or other mechanisms may also improve motor function after spinal cord injury or stroke are also envisioned. Those skilled in the art may envision other neuromodulation indications for visceral organ neuromodulation, such as cardiac function.

Figure 2:
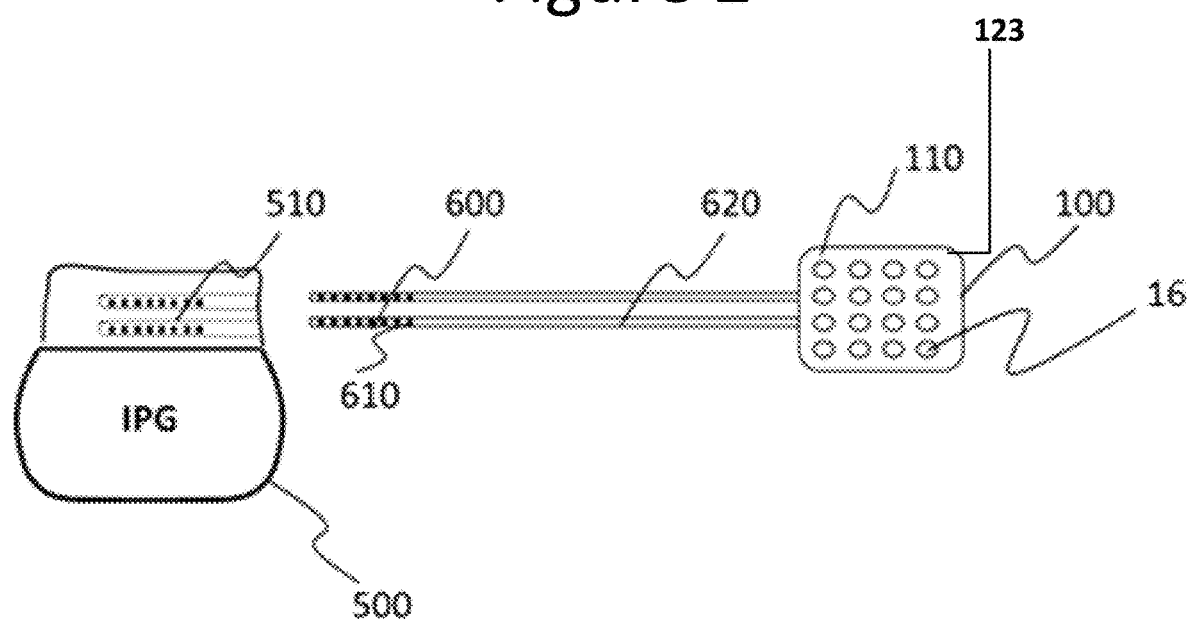
FIG. 2 diagrammatically shows one embodiment of an implantable therapy array, connection leads, and IPG.

FIG. 2 schematically shows an implantable neuromodulation system for stimulation therapy configured in accordance with illustrative embodiments. As shown, an implantable stimulation system 100 contains an electrode array 110 (also called a "therapy array 110") with one or more stimulation contacts 16. An IPG 500 connected to the electrode array 110 delivers current or voltage mode waveforms to one or more array contacts 16. The IPG 500 may be configured to deliver one or more therapy pulse types (e.g., tonic 50 Hz, 200 microseconds; sub-perception/high-rate 1-50 kHz; burst pulses 200 microsecond pulse train) to the neural tissues. Pain relief therapy may be provided in the form of sub-perception or paresthesia based benefit.

The IPG 500 typically has an energy source (battery) and control circuit that determines the energy sent to each electrode array 110. The IPG 500 may have one or more connection ports 510 to connect the electrode array 110. The implantable system 100 delivers therapy to neural tissues with the electrode array 110 and the IPG 500 via and at least one lead body 620, with proximal connector contacts 610. The electrode array 110 may also contain embedded electronics (active switch matrix, multiplexer, or other control circuit) for communicating with the control circuit in the IPG 500. The IPG 500 can be charged wirelessly and communicate with an external device to establish the active stimulation contacts, amplitudes, or pulse patterns.

The IPG 500 directs electrical stimulation patterns to one or more contacts 16 within the electrode array 110 individually/independently or in combination for current-shaping or current-steering. The IPG 500 may also record neural signals or other physiological signals to inform the delivery of therapy (for example, in a closed loop fashion).

As noted above, the electrode array 110 has one or more stimulation contacts 16 formed within a substrate 123. In one embodiment, the electrode array 110 may be organized in rows and columns of contacts 16 in an array type configuration for delivering stimulation at multiple points along the neural tissue. Multiple contacts 16 provide the opportunity to deliver stimulation from contacts 16 or groups of contacts 16 to steer therapy to the desired dermatome, while not stimulating other dermatomes (see below). Among other shapes and sizes, the contacts 16 may be round, oval, or rectangularly shaped or approximately 1-2 mm wide and 2-5 mm in length when used for epidural spinal cord electrical stimulation embodiments. Moreover, the contacts 16 may be flat or not flat, and have an electrical impedance of between 200 and 1000 ohms.

Spinal Anatomy

FIG. 3 shows a mid-sagittal view of the spinal cord 14 within the vertebral segments 10, as well as the spinal nerves 22, which exit through the intervertebral foramen 36 of the spinal column 11. The spinal column 11 is sectioned into 4 regions, the cervical 48, thoracic 50, lumbar 52, and sacral 54 in descending order from the brain. Illustrative embodiments provide therapy to the spinal cord 14 at one or more of these regions. Each of the vertebra 10 within these regions are numbered (C1-C7 48, T1-T12 50, L1-L5 52, S1-S5 54)

and have corresponding spinal nerves 22 that enter the spinal cord 14 through the respective intervertebral foramen 36.

FIG. 4 shows an isometric view of the spinal cord 14, with bundles of ascending or afferent and descending or efferent nerve fibers that carry sensory and motor signals to and from the brain, respectively. The spinal nerves 22 separate into the dorsal spinal branch, which contains the ascending, sensory nerves, and ventral spinal branch, which contains the descending, motor nerves. The dorsal branch contains the dorsal root ganglion 20, the collection of afferent nerve cell bodies, and forms the dorsal roots and rootlets (both identified by reference number "24"), which enter the spinal cord 14 through the dorsal root entry zone 28 via the dorsal horn 26, as described below.

Those skilled in the art will be familiar with gate-theory and other therapeutic mechanisms of spinal cord stimulation. To provide pain relief using neurostimulation, the pain information carried through neural circuits is believed to be inhibited in the dorsal horn. This may be achieved by stimulation of an afferent, peripheral nerve, the dorsal root ganglion 20, a dorsal root 24, the dorsal root entry zone 28 (aka "DREZ 28"), or a fasciculus of the dorsal columns 18. Spinal nerves 22 enter the spinal column 11 via the intervertebral foramen 36 (FIG. 6, discussed below) after which they split into the ventral and dorsal roots 24, which have motor and sensory function, respectively. Sensory signals continue through the dorsal root ganglion 20 (FIG. 4) and the proximal process carries these signals via the dorsal roots 24 to the synaptic terminus at the dorsal horn 26 within the spinal cord 14. The area where the dorsal rootlets 24 enter the spinal cord 14 is known as the dorsal root entry zone 28. The nerve fibers of the dorsal roots 24 become incorporated into the lateral edge of the dorsal column 18. As the fibers ascend toward the brain, the fibers from the caudal dermatomes (inferior fibers) move medially within the dorsal column 18 to allow for incorporation of the fibers joining from the nerves of the upper body (superior fibers). In the cervical region 48, there are two structures, the gracile fasciculus 30 and the cuneate fasciculus 32, which are composed of these inferior and superior fibers, respectively. The therapy array 110 may be positioned at the appropriate vertebral and medio-laterally level to provide stimulation to the desired dermatome.

Epidural Space Anatomy

For successful spinal cord stimulation, the epidural space 12 facilitates the electrode array 110 and stimulation contacts 16 positioned in the vicinity of the targets of interest in a manner that results in lower energy stimulation and greater selectivity. The paddle-type electrode array 110 preferably occupies the epidural space 12 to prevent movement or lead migration. Simultaneously, in illustrative embodiments, the volume, geometry, and stiffness/flexible properties of the electrode array 110 preferably do not cause spinal cord compression, dorsal root compression, or spinal cord injury.

Figure 6:
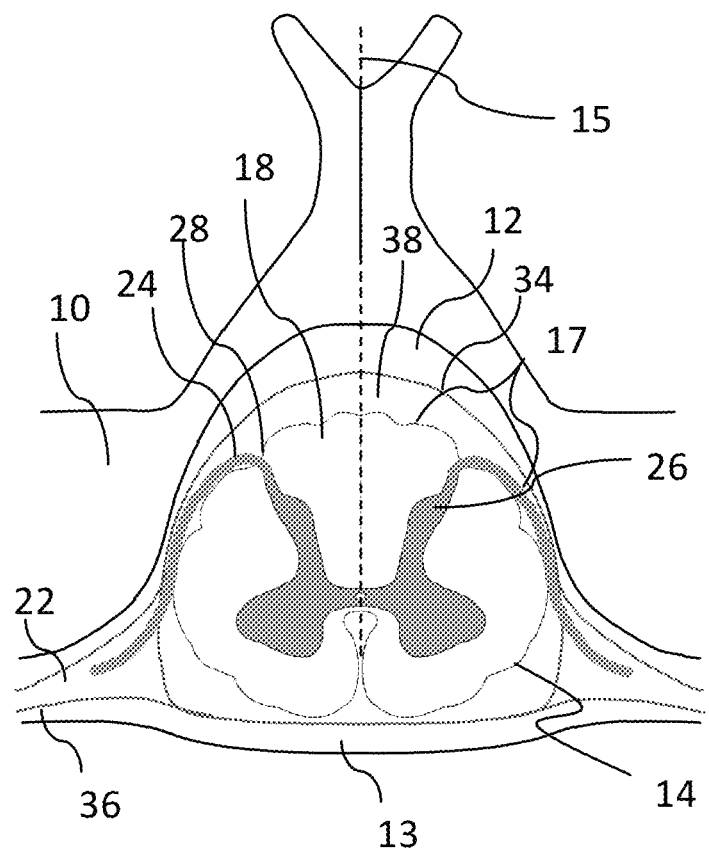
FIG. 6. diagrammatically shows the spinal column illustrating the details of the bone structure surrounding the spinal cord, the shape of the epidural space, and the meningeal layers.

FIG. 6 shows a cross-sectional view of the lateral epidural space 12. As known, the spinal cord 14 is positioned medially within the foramen 13, is protected by the dura mater 34, and floats within the subarachnoid space 38, which is filled with cerebrospinal fluid 38. In this case, the vertebral foramen 13/36 may be considered a "normal vertebral foramen" because thought it has been surgically modified for access, it has not been geometrically altered to receive/ make space for the volume of the therapy array 110. In other words, the portion of the foramen 13/36 adjacent to the dorsal root 24 and other relevant anatomy is in its substantially natural state.

At anatomical midline 15 of the spinal cord 14 on FIG. 6, the epidural space 12 is the thickest (typically approximately 4 mm). However, the epidural space 12 progressively narrows above the lateral spinal cord tissues (cuneate fasciculi 32, dorsal root 24, dorsal root entry zone 28) and toward the pedicle 58. Similarly, the subarachnoid space 38 and cerebrospinal fluid thickness are the greatest at anatomical midline (approximately 2-4 mm at the thoracic level and 1-3 mm at the cervical level) and thinner laterally (less than 2 mm at both the thoracic and cervical levels).

The noted clinical complications of prior art electrode arrays positioned in the lateral epidural space 12 includes compression injury to the dorsal roots 24 and/or chronic pain or loss of therapy. Compression of the nerve roots 24 adjacent to the pedicle 58 occurs due to the geometric volume and stiffness mismatch of these regions with prior-art electrode arrays. Furthermore, mechanical compression gives rise to lower excitation threshold of nerve roots 24, which, as noted above, may reduce the overall therapeutic benefit.

Figure 7:
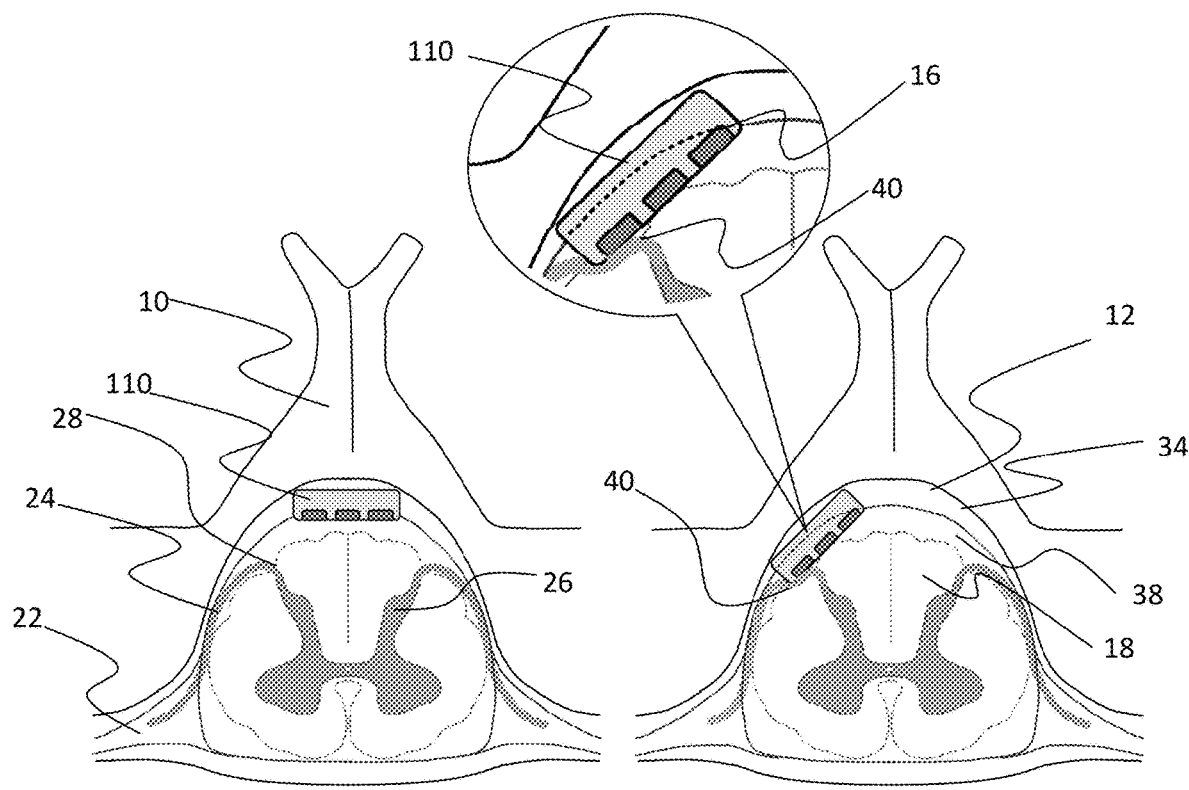
FIG. 7 diagrammatically shows a placement of two stimulation electrode arrays within the epidural space positioned medially (left figure) and laterally in a medically compressed manner (right figure) on the spinal cord.

Prior art multi-contact electrode arrays produced for anatomical midline positioning often have a thickness of approximately 2 mm, a width of less than about 10 mm, and a length from 15-65 mm. FIG. 7 left illustrates how prior-art electrode array substrates undesirably can apply pressure on the dura mater 34 at the anatomical midline and compress the cerebrospinal fluid ("CSF") without compressing the spinal cord 14. Prior-art electrode arrays have optimized relatively stiff substrates with a thickness of approximately 2 mm for medial placement, with the stiffness intended to prevent lead migration movement. As shown in the figure, with a midline placement, the electrical contacts 16 cannot locally access the lateral neural tissues, such as the cuneate fasciculus 32, dorsal root entry zone 28, and/or dorsal roots 24.

Those prior-art flat or curved electrode arrays cannot be readily advanced laterally within the epidural space 12 near the dorsal root entry zone 28 or the pedicle 58 due to the narrow volume and curvature of the spinal anatomy. FIG. 7 illustrates the cross section of a plate-type electrode array 110 positioned at the anatomical midline (left) and a lateral position (right) adjacent to the dorsal root 24 and pedicle 58. When the electrode is advanced laterally (right), a compression zone 40 undesirably forms where the CSF, dorsal root 24, and/or lateral dorsal columns 18 may become impinged by the electrode volume. FIG. 7 (right) illustrates the medically-compressed condition where a prior art therapy array compresses the CSF, the dorsal root 24, and the lateral dorsal columns 18 adjacent the pedicle 58. To illustrate this phenomenon, a dashed line through the therapy array shows the compressed tissue before implantation. For example, that compression may be greater than 1.2 mm (e.g., 1.5 mm) Illustrative embodiments mitigate this problem.

Pre-operative surgically assessment of the vertebral foramen 13/36 and epidural space 12 volume restrictions are performed as standard of care (e.g., MRI, CT, or other imaging) to facilitate surgical risk analysis, planning, and electrode array selection. A narrow epidural space risk would likely preclude placement of prior art paddle electrode arrays and use of a percutaneous cylindrical electrode with a lower volume, causing a reduced therapeutic benefit. Those skilled in the art recognize that the dorsal column 18, the dura mater 34, and the dorsal root extradural width, radius of curvature, and mechanical properties are different in the thoracic, cervical, lumbar, and sacral regions. Similarly, the inventors recognized that the dura mater 34 is also different, requiring a flexible, conformal, and non-compressive geometry to accommodate multiple vertebral level geometries. Illustrative embodiments of the invention overcome these limitations and enable a paddle electrode array to be implanted laterally near one or more pedicles 58, thus opening an entirely new therapeutic benefit for those in need of therapy.

Surgical Procedure

A standard of care surgical procedure typically begins with an initial incision and a subperiosteal dissection down to the lamina near the vertebral segment 10 of interest. The electrode array 110 is surgically placed by removing part of the vertebral segment 10 (laminotomy/laminectomy) at the cervical 48, thoracic 50, lumbar 52, or sacral regions 54 of the spinal cord 14. The ligamentum flavum is then removed and vertebral foramen 13/36 is exposed but not altered, thus leaving it in its natural state. Epidural fat and other tissue is cleared from the epidural space 12, taking care to avoid pressure on the spinal cord 14. The electrode array 110 is inserted within the epidural space 12 in a manner to avoid putting pressure on the spinal cord 14 during placement.

After the electrode array 110 is positioned in the epidural space 12, the rostro-caudal position may be optimized by advancing the electrode array 110 longitudinally. Frequently, the electrode array 110 is removed to clear additional tissue to facilitate positioning. Adjustments at the anatomical midline may be accommodated without causing compression on the dorsal roots 24, or other neuronal tissues laterally within the spinal cord 14. Illustrative embodiments overcome the noted surgical and anatomical limitations inherent in prior-art methods and technologies by providing a method that does not compress the required neural tissues, providing effective therapeutic stimulation of neural tissues to alleviate pain within a sub-region of a patient's body.

Selectivity of Therapy to Dorsal Columns and Dorsal Roots

Figure 8:
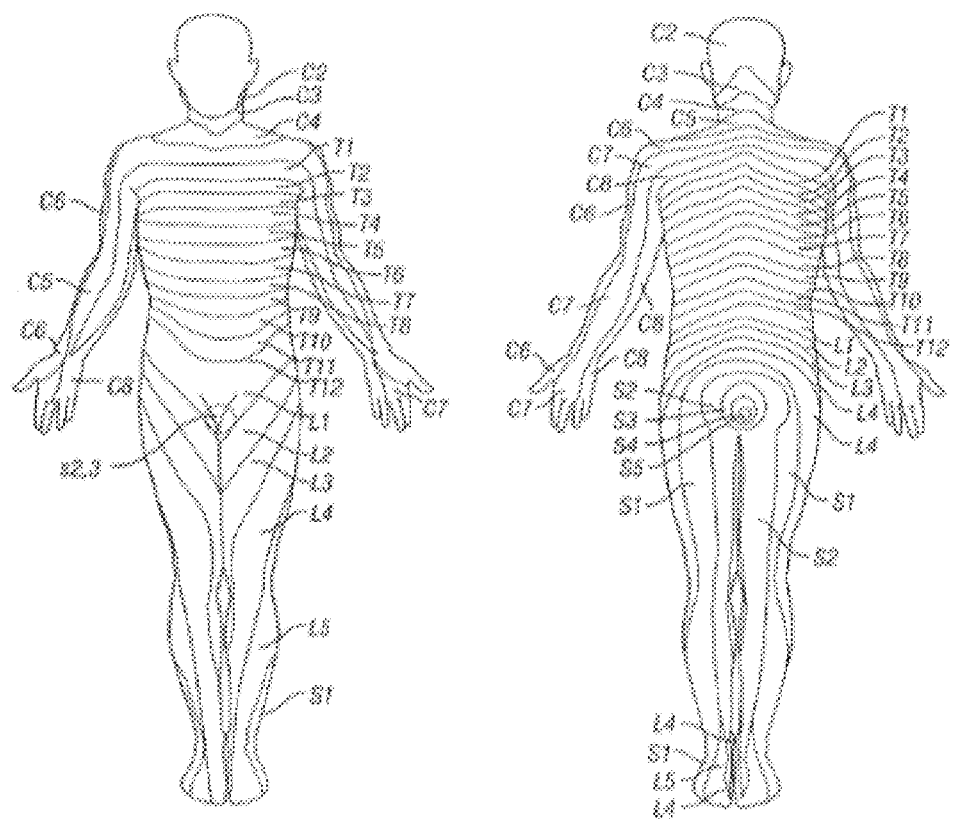
FIG. 8. shows the dermatomal map of the human body and illustrates the connections between sensing regions and the related spinal nerves.

Those skilled in the art recognize that the dermatomes are somatic or musculocutaneous areas served by fibers from specific spinal nerves 22, as shown in FIG. 8, with the corresponding spinal nerves shown in FIG. 3. The dorsal columns 18 are a tract of ascending fibers carrying pain and other information to the brain, which may be stimulated anatomically to inhibit pain. Similarly, the dorsal roots 24 carry sensory information from the organs and other regions of the patient's body to the brain and also may be stimulated. Prior art electrode arrays known to the inventors have focused on stimulating one or more fibers or fasciculi within the dorsal column 18, while seeking to avoid off-target activation of other dorsal column 18 or the dorsal roots 24. As described above, the material stiffness and bulk volume of prior-art electrodes (both flat and curved geometries) prevents contacts from being positioned adjacent to the lateral neural tissues or the dorsal roots 24 without mechanical compression complications (FIG. 7) and loss of therapy.

Figure 9:
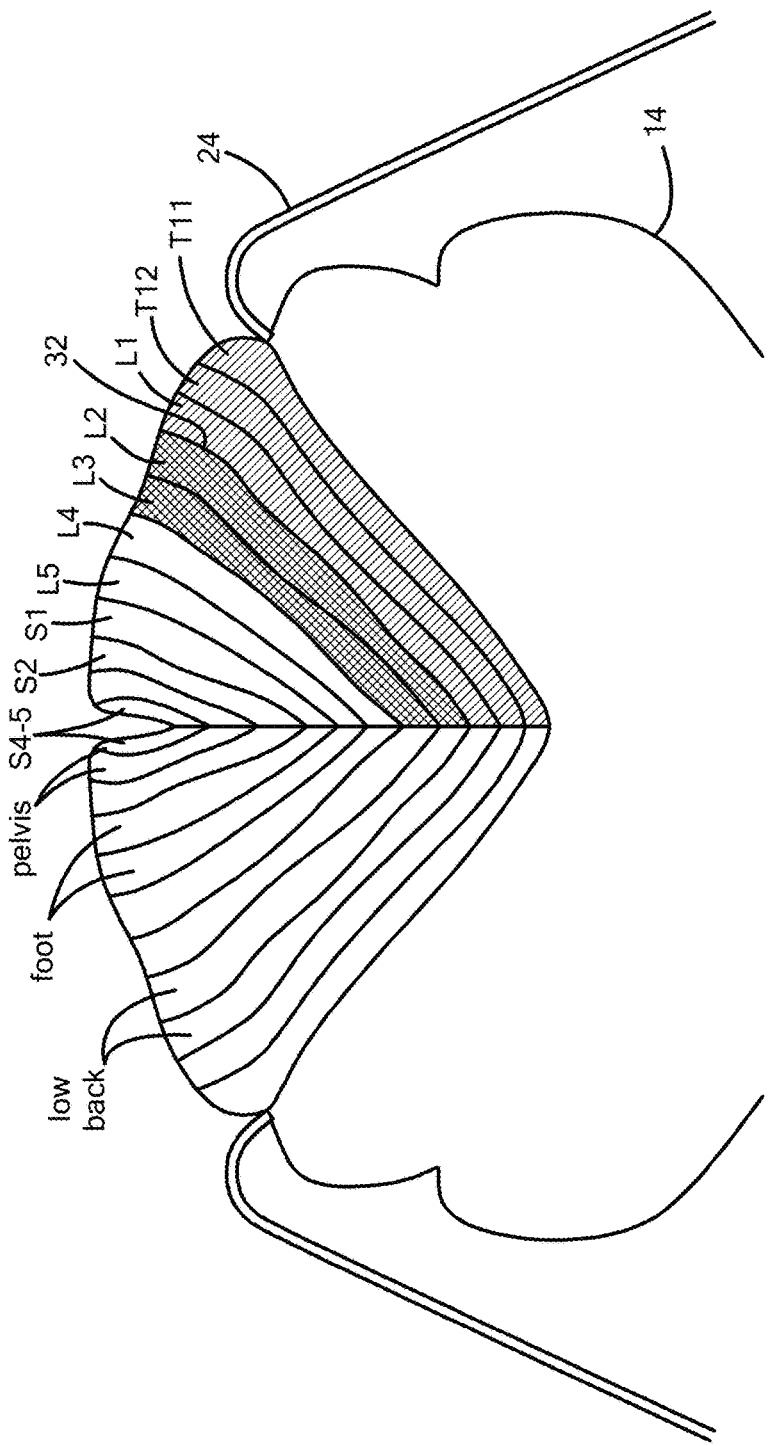
FIG. 9. diagrammatically shows a cross section of the dorsal column at T10 and identifies the location of the subset of nerve fibers within the dorsal column associated with each of the spinal nerves that have joined the dorsal column.

For discussion purposes, FIG. 9 illustrates a cross-section of the dorsal column 18 (taken at the T10 vertebral level) and the position of ascending fibers that connect to the respective dermatomes, as well as the nerve roots. Similarly, the dorsal roots 24 enter the spinal cord 14 at the dorsal horn via the dorsal root entry zone 28 and convey signals from the periphery. The dorsal roots 24 and the dorsal root entry zone 28 also represent an anatomical location in which stimulation therapy array 110 may be positioned to selectively provide therapy to one or more sub-regions of the patient's body.

Considering the dorsal column anatomy at the T10 vertebral level as an example, the lateral-most positioned fibers within the column correspond to the T11-L2 dermatomes. As shown in FIG. 8, these dermatomes represent the axial low-back region of the body. Therefore, to provide therapy for axial low back pain, an electrode at T10 optimally stimulates the lateral fibers of the dorsal column 18 adjacent to the nerve roots and pedicle 58. In one embodiment of the invention, the electrode array 110 positioned laterally near the pedicle 58 with one or more contacts 16 configured to deliver stimulation selectively or in combination to the lateral dorsal column 18, dorsal roots 24, or dorsal horn to provide pain relief to a sub-region of the patient's body. Accordingly, illustrative embodiments enable greater selectivity in stimulating the dorsal root 24 and the dorsal column 18.

Figure 10:
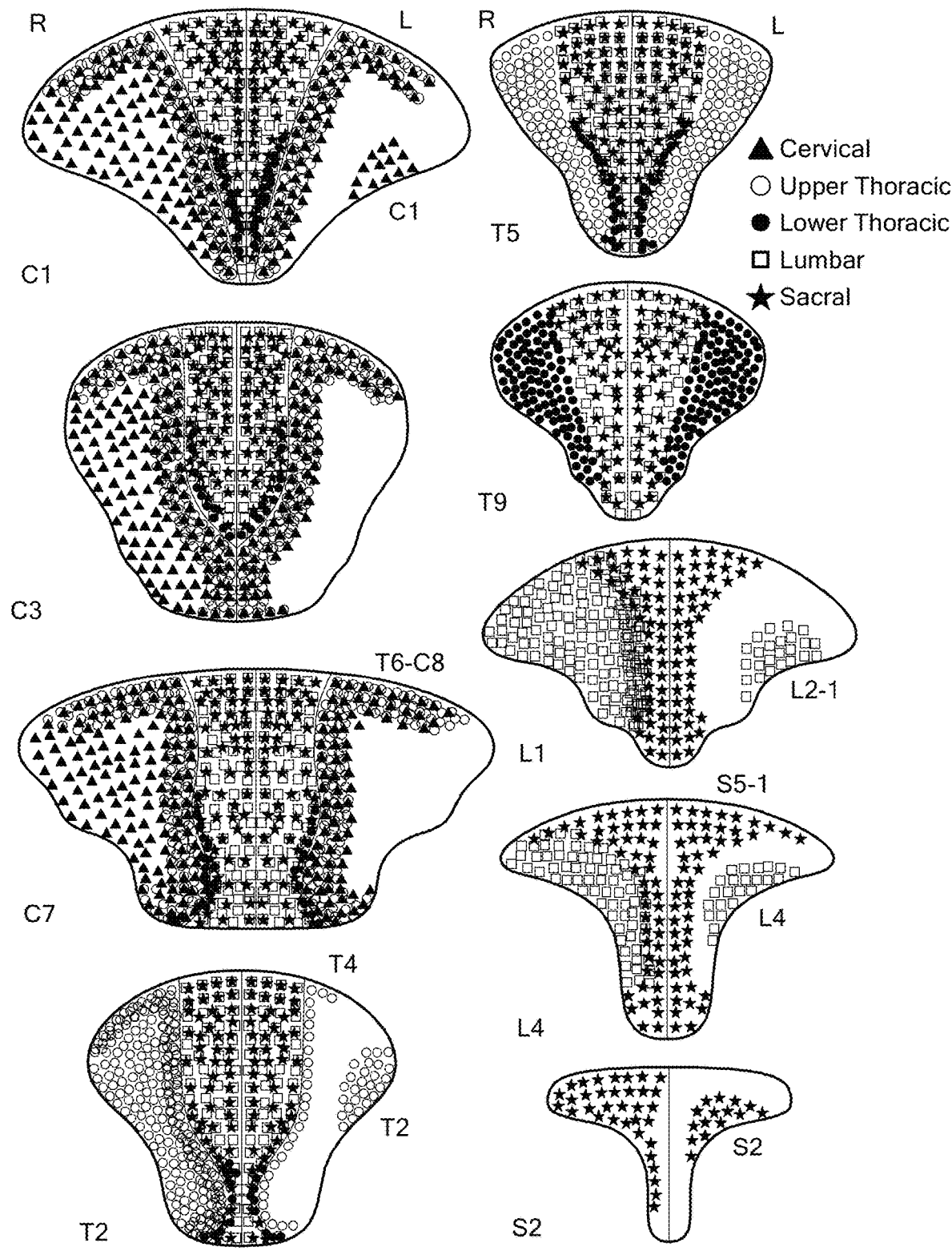
FIG. 10 diagrammatically shows cross sections of the dorsal column at multiple vertebral levels ranging from the cervical to the sacral and illustrates how merged nerve fibers move medially as they ascend the spinal column. Where available, the segmental origins of fibers are indicated.

Those skilled in the art recognize that the position of axonal nerve fibers in the dorsal column 18 corresponding to a specific dermatome move medially with each change in vertebral level 10. FIG. 10 shows a depiction of the dorsal column cross-sections at multiple vertebral levels along with the relative position of the cervical 48, thoracic, 50, lumbar 52, and sacral 54 fasciculi or tracts (bundles of axons).

Accordingly, in illustrative embodiments, a method stimulates one or more lateral neural structures of the spinal cord 14 (e.g., one or more of lateral fibers of the dorsal column 18, dorsal roots 24, dorsal root entry zones 28, dorsal horns 26) by implanting the electrode array 110 at an effective location and in an effective manner. To that end, the electrode array 110 may have one or more substrate regions that each has a prescribed set of thickness and stiffness properties. Preferably, the method enables implantation in a medically uncompressed manner; namely, the method implants in a manner that does not non-negligibly mechanically compress or irritate the dorsal roots 24 or spinal cord 14 in the patient. For example, various embodiments do not compress the dura mater 34 and/or cerebrospinal fluid more than 1.2 mm after implantation, thus mitigating abnormal dorsal root activation. The method also selects one or more contacts 16, and delivers one or more stimulation pulse patterns to the sites to preferentially stimulate at least one of the dorsal roots 24 and/or at least one of the dorsal columns 18 to provide therapy associated with a sub-region of the patient's body.

Figure 11:
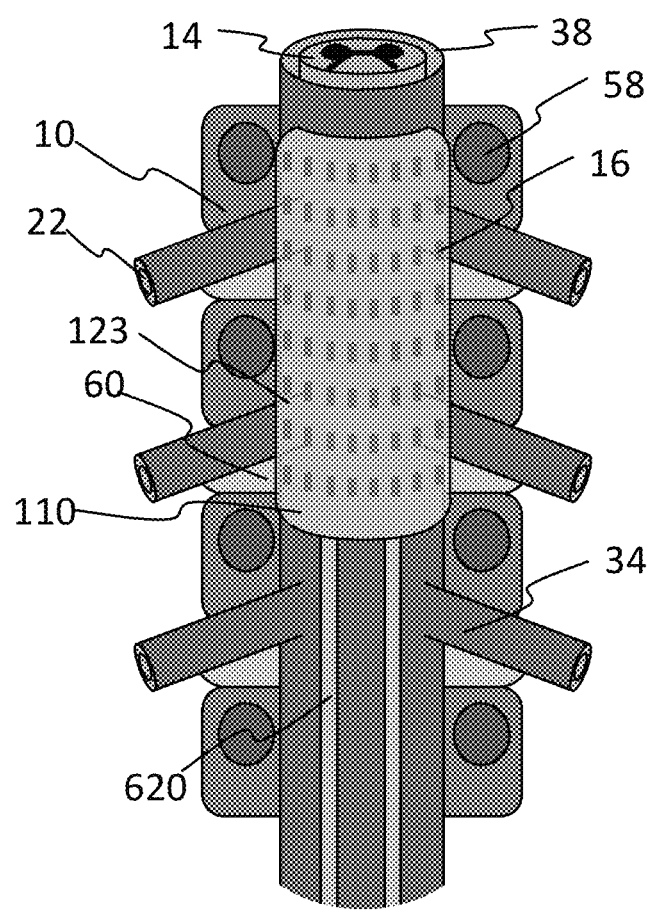
FIG. 11 diagrammatically shows conformal placement of a therapy array within the epidural space on the dura mater and spanning from left to right pedicle in accordance with one embodiment. The array extends longitudinally approximately 2 vertebral levels. The vertebral arch, transverse process, and spinous process have been removed for clarity.

FIG. 11 shows a coronal perspective of the conformal electrode array 110 positioned extradurally to the spinal cord 14 with multiple contacts 16 and at least one lead body 620. As shown, the dorsal roots 24 exit the spinal cord 14 through the intervertebral foramen 13/36 between the pedicle 58.

In preferred embodiments, the substrate 123 (aka "body") of the electrode array 110 is flexible and conformable to the dura mater 34. For example, the substrate 123 has mechanical properties so that when implanted, its topology and shape in its X-Y dimension (its planar top and bottom sides) are controlled by the shape of the surface(s) of the dura mater 34 (i.e., the electrode array 110 is conformal to the dura mater 34). While some substrate regions are uncompressed, some substrate regions may cause some compression. For example, the substrate 123 may have at least one set of sub-region(s) with a thickness (e.g., between 0.1 mm and 1.5 mm) and stiffness/flexibility properties (e.g., 0.1 MPa to 1000 MPa) that enable the safe positioning of stimulation contacts 16 at the anatomical midline, which may optionally compress the dura mater 34 and CSF 38. For further functionality, the flexible substrate 123 also may be configured to be curved on at least two parallel or perpendicular axes.

It should be noted that ranges of between X and Y herein are considered to include the end points. Thus, the substrate sub-region noted above with a thickness between 0.1 mm and 1.5 mm should be considered to include substrates 123 that are 0.1 mm and 1.5 mm.

The various sub-regions of the electrode array 110 contain one or more contacts 16, and the lateral edges of the array 110 may be located adjacent to the pedicle 58 with contacts 16 to stimulate the dorsal roots 24 and lateral dorsal neuronal tissue 18. Unlike another embodiment that may be mounted either in a compressed manner or uncompressed relative to the midline, the mechanical properties of one or more of these other sub-regions of the electrode array 110 enable the stimulation contacts 16 to be positioned laterally adjacent to the dorsal roots 24 and pedicle 58 on the left and/or right side in a medically uncompressed manner. Thus, various properties of the substrate 123 enable safe implantation adjacent to at least one pedicle 58 and/or at least one dorsal root 24 in a medically uncompressed manner. Referring to FIG. 11, stimulation contacts 16 are shown extending from the right dorsal root 24 and pedicle 58 across the anatomical midline to the left dorsal root 24 and pedicle 58. In another embodiment, the substrate 123 may disperse stimulation contacts 16 between one pedicle 58 and the anatomical midline.

Figure 12:
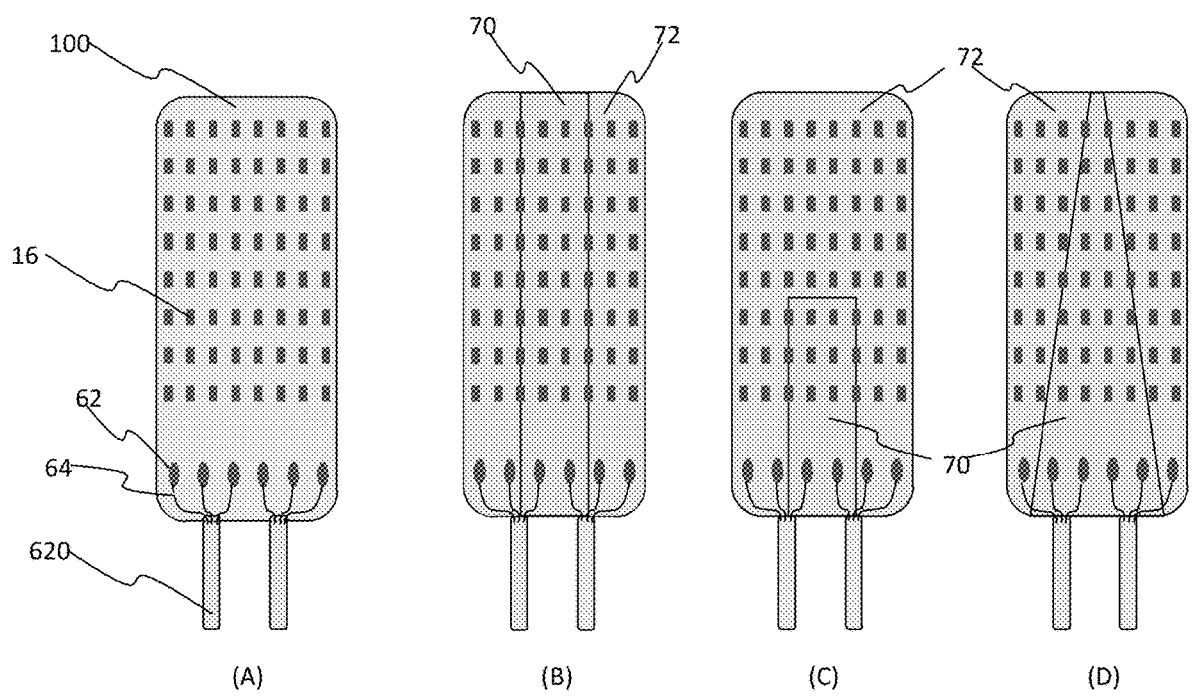
FIG. 12 schematically shows a top down view of several embodiments of an uncompressive therapy array with a thin, conformal edge or edges containing contacts and may be thicker in one or more sections not at the edges. A: a uniform thickness therapy array. B: a therapy array with uniform cross section along the longitudinal direction. C: a therapy array with a uniform cross section on the proximal end and a different, uniform cross section on the distal end. D: a therapy array with a cross section which changes as a function of distance along the longitudinal direction.

FIG. 12 shows several embodiments of the electrode array 110 with one or more sub-regions, where each sub-region has an associated thickness and stiffness and electrical contacts 16. In one embodiment (FIG. 12, (a)), the substrate 123 conforms to the entire surface of the dura mater 34, and the substrate thickness is generally uniformly less than 2.0 mm (e.g., 0.1 mm-1.5 mm, 0.2 mm-1.0 mm, 0.3 mm-0.8 mm, 0.1 mm-1.2 mm, or 0.2 mm-1.2 mm) and may have a generally uniform flexibility. At midline, the dura and CSF facilitate moderate compression (1-3 mm). In another embodiment (FIG. 12, (b)), a multi-regional substrate 123) a first sub-region 70 containing contacts 16 is optimally positioned at the anatomical midline to prevent lead migration and to optimize coupling. A second sub-region 72 contains electrical contacts 16 and has a prescribed thickness and stiffness to implant the substrate 123 laterally (FIG. 11) in a medically uncompressed manner adjacent to the pedicle 58 and dorsal roots 24. The first sub-region may be between 0.1 mm and 1.5 mm in thickness, while the second sub-region 72 is normally between about 1.0 mm and 2.0 mm. One of the sub-regions may have greater mechanical stiffness properties than the other sub-regions to facilitate positioning and to prevent lead migration For example, the first sub-region 70 may be stiffer (e.g., 0.1 MPa to 1000 MPa) than the second sub region 72 (e.g., 1 MPa to 10 GPa). For example, the first sub-region 70 may have a stiffness of 0.5 MPa or 0.9 MPa and the second sub-region 72 may have a stiffness of 1 MPa or 100 MPa. Of course, in other embodiments, the substrate 123 may have a substantially constant stiffness, such as a stiffness between 0.1 MPa and 10 MPa. Different thicknesses discussed herein may be paired with the respective stiffness amounts discussed in this and other paragraphs.

Similarly, FIG. 12(c) depicts other sub-region configurations in which sub-regions of the therapy array 110 contain welding receiving pads 62 and contacts 16, to enable the implantation of the substrate 123 in a medically uncompressed manner. In some embodiments, the substrate 123 may have regions of thickness between 0.1 mm and 1.5 mm (e.g., 0.1, 0.25, 0.5, 0.75, 1.0. 1.25, or 1.5 mm). Some embodiments may have a thickness between 1.5 mm to 3.0 mm.

Figure 13:
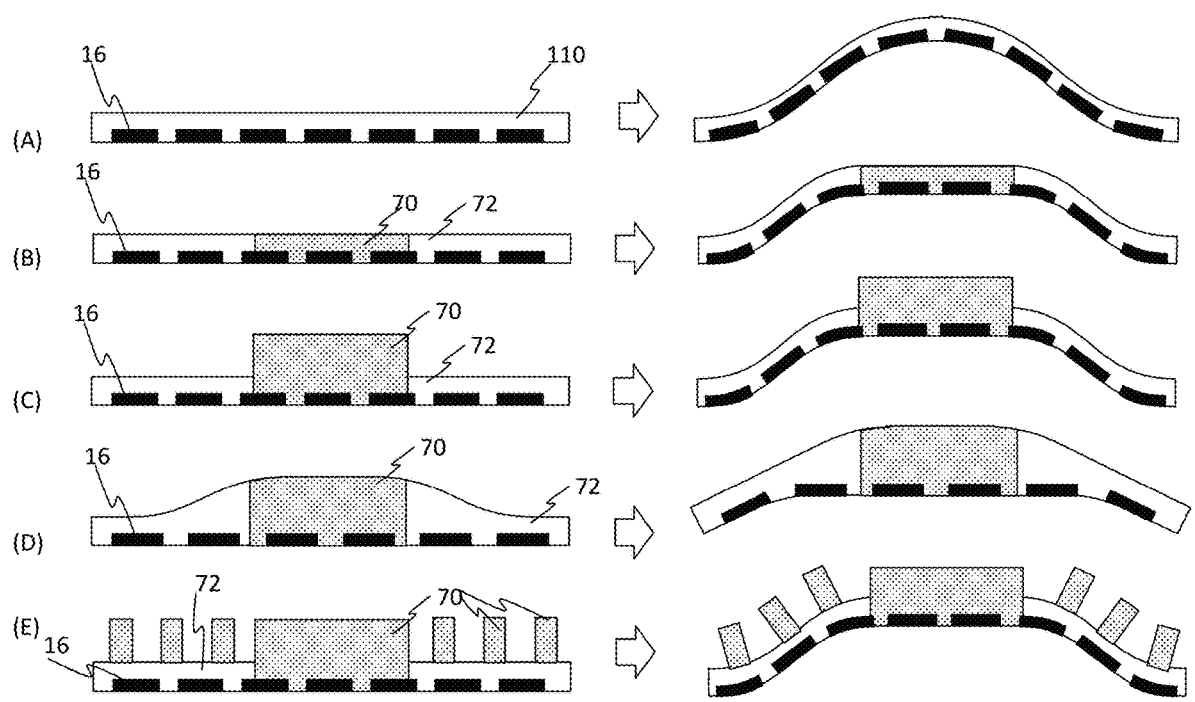
FIG. 13 shows schematically (Left column) several embodiments, in cross section, of a non-compressive therapy array having thin, conformal edge regions containing contacts and may be thicker along the midline, which also contains contacts. A: an electrode array with a uniform cross section. B: an electrode array with a discrete midline section substantially stiffer than the edge. C: an electrode array with a discrete midline section substantially thicker than the edge which may also be substantially stiffer. D: an electrode array where the thin edge sections transition smoothly into a substantially thicker and possibly stiffer midline section. E: an electrode array with an alternating thin, thick structure. Right column: examples of conformal mapping of these embodiments of the therapy array to curved surfaces such as the dura mater.

FIG. 13 schematically shows cross-sectional views of the substrate 123 in accordance with various different embodiments. The left side depicts thickness and conformal properties that enable positioning adjacent to the pedicle 58 and dorsal roots 24 in a medically uncompressed manner—and conforming to the dura mater 34. In one embodiment, one or more sub-regions may have the same thickness (a) or different material thicknesses (c). In another embodiment, the sub-regions may have a different stiffness (b). In still another embodiment (c), the transition between two sub-sections is step-wise. In yet another embodiment, the transition between sub-sections is gradual, such as continuously arcuate (d). Another embodiment (e) has multiple sub-regions with multiple transitions.

The right side of FIG. 13 schematically shows how the substrate 123 may conform to the dura mater 34 after implantation, where the electrical contacts 16 are disposed in at least one sub-region of the substrate 123. In preferred embodiments, the contacts 16 are at least in the most flexible and thinnest sub-region(s). It should be noted that features of various embodiments shown in FIG. 13 may be combined in a single substrate 123. Accordingly, discussion of one of those embodiments is for discussion purposes and not intended to limit various other embodiments of the invention.

Figure 14:
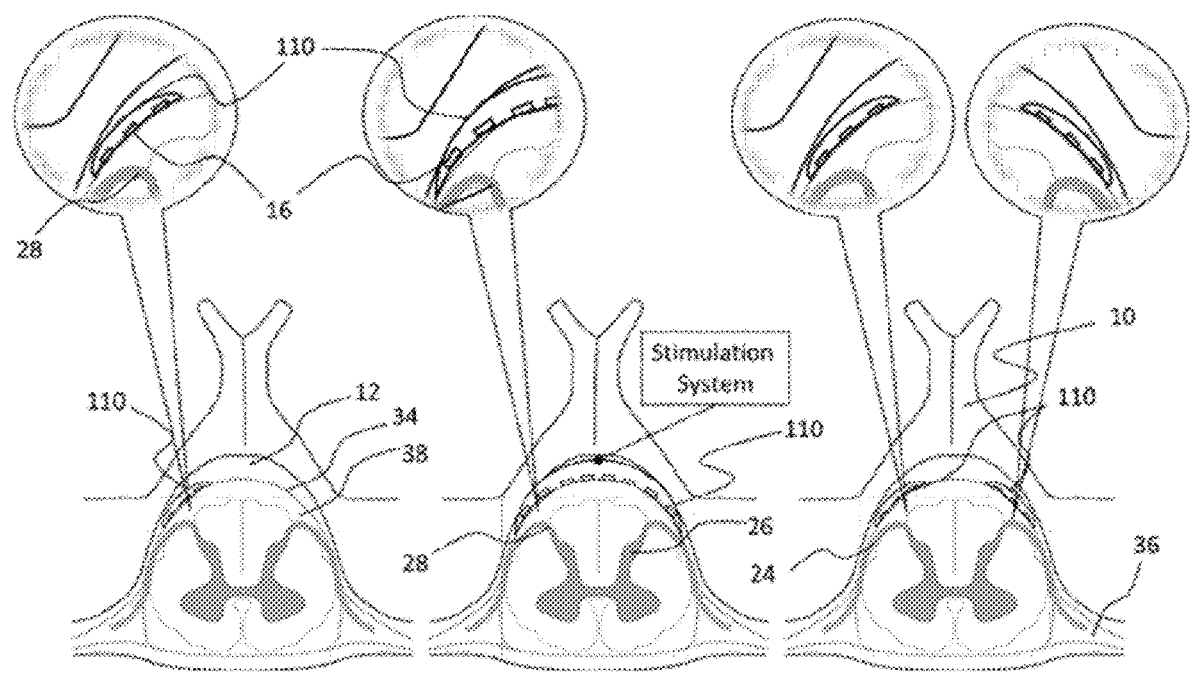
FIG. 14 schematically shows a non-compressive electrode array delivered to a subset of neural tissues without compression (top row, callouts) in illustrative embodiments. Therapy may be delivered to (bottom): one lateral dorsal root or lateral fasciculi (left), the left and right dorsal root and all intervening neural tissues (middle), and at least one dorsal root or lateral fasciculi on either side of the midline (right).

FIG. 14 shows three different mounting configurations in accordance with illustrative embodiments. All three have laterally placed therapy arrays 110 and are mounted laterally in the medically uncompressed manner discussed above. All three also show the laterally placed array 110 coupled adjacent to certain fasciculi, dorsal roots 24, and dorsal root entry zones 28. As such, using the independently acuatable contacts 16 of the array 110, illustrative embodiments may stimulate specific fasciculi, dorsal roots 28, etc. either together, separately, or in certain combinations.

The left figure shows lateral placement only (only one side), while the right figure shows bilateral placement (lateral placement on the two sides). The middle figure shows placement across substantially the entire span of the epidural space 12 (i.e., from end to end of the epidural space 12 between the two dorsal root entry zones 28). This latter embodiment provides both medial and lateral stimulation.

As shown, the lateral edge of the substrate 123 is adjacent to the pedicle 58, and the contacts 16 are positioned near at least one lateral neural structure of the spinal cord 14. In these embodiments, the therapy array 110 and its contacts 16 are arranged preferentially adjacent to dorsal roots 28, dorsal root entry zones 28, and lateral dorsal columns 18 for selective stimulation. Electrodes 16 are also extended across the dorsal columns 18 spanning between pedicles 58, to provide therapy to at least one sub-region of the patient's body. As with other embodiments, the electrode array 110 of these embodiments has one or more substrate sub-regions with thickness and stiffness properties that facilitate conforming to the dura mater 34 after implantation in a medically uncompressed manner (i.e., to not mechanically compress or irritate the dorsal roots 24 or spinal cord 14 in the patient).

As shown in the FIG. 14, the dorsal roots 24 and the lateral CSF are not medically compressed by the presence of the therapy array 110. To that end, the top surface of the therapy array 110 (i.e., the side facing upwardly/outwardly from the perspective of the cross-sectional view of FIG. 14) may be spaced from the top of the epidural space 12. Other embodiments may position the top and bottom surfaces of the therapy array 110 to contact the top and bottom of the epidural space 12.

The method of stimulation may be applied to a subset of the lateral dorsal columns 18 to provide "therapy" to an associated sub-region of the patient's body. Therapy is primarily identified as providing electrical stimulation (e.g., a prescribed current) to treat chronic pain, although other embodiments may treat motor function deficits, headaches, or urinary tract dysfunction, among other things. In another embodiment, the method of stimulation is applied to one or more dorsal roots 24 or the dorsal root entry zone 28 to provide therapy to one or more associated sub-regions of the patient's body. In another embodiment, the method of stimulation is applied to a combination of dorsal columns 18 and dorsal roots 24.

As noted above, one embodiment of the invention includes an electrode array 110 with one or more conformal sub-regions, and each region has a prescribed thickness and stiffness. The array 110 may be advanced and implanted within the lateral epidural space 12 with the lateral edge of the substrate 123 adjacent to the pedicle 58 in a medically uncompressed manner as shown in FIG. 14 (left), with contacts 16 positioned adjacent to lateral fibers of the dorsal column 18, the dorsal roots 24, and/or the dorsal root entry zones 28 to deliver stimulation. One or more stimulation contacts 16 and stimulus waveforms may target the dorsal roots 24 or the lateral dorsal columns 18 associated with one or more sub-regions of the patient's body as described using electric field modeling below.

Referring again to the embodiment of FIG. 14 (middle), the electrode array 110 may be advanced within and positioned from the anatomical midline in both directions. In this embodiment, both lateral edges of the substrate 123 may be positioned adjacent to the pedicle 58 in a medically uncompressed manner, with electrodes near the lateral fibers of the dorsal column 18, the dorsal roots 24, and the dorsal root entry zones 28, and any medial-lateral fibers of the dorsal column 18. In one example, the electrode array 110 is conformal with one or more sub-regions having a prescribed thickness and stiffness to match the epidural space geometry without compressing the dorsal roots 24 of the spinal cord 14. The method provides therapy to one or more sub-regions of the body associated with any lateral dorsal roots 24, dorsal root entry zone 28, or medial-lateral neural tissues and roots of the spinal cord 14.

Figure 15:
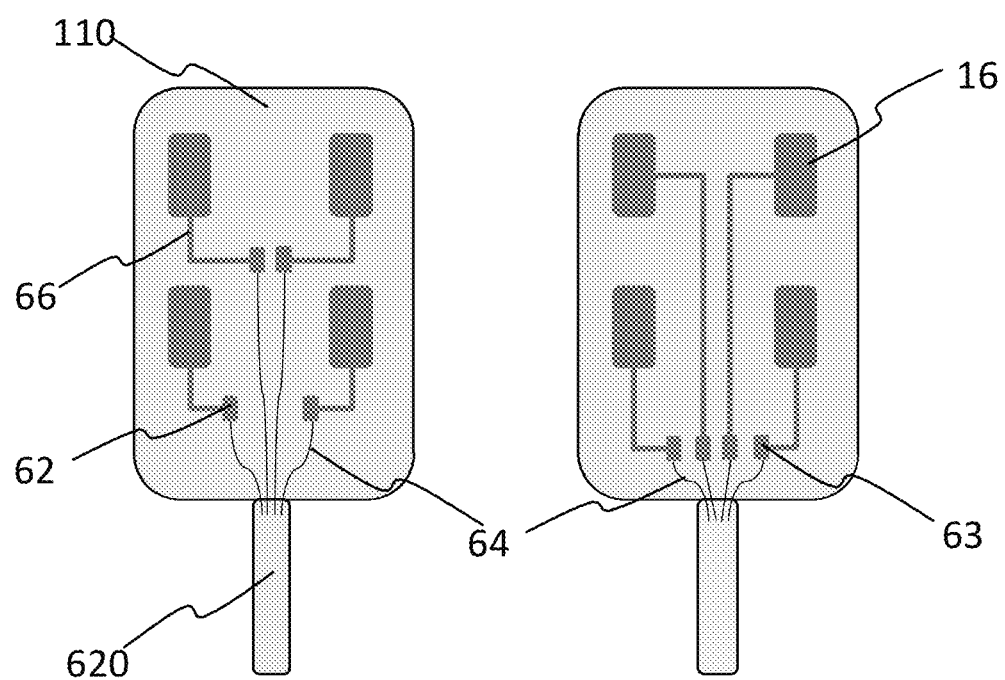
FIG. 15 schematically shows two depictions of a plurality of embodiments of continuous, conductive elements within an electrode array. Wires or other conductive elements may be joined to these continuous, conductive elements at connection points within the array.

In another embodiment of the invention, continuously conductive elements 66 may enable contacts 16 to be positioned within certain sub-regions of the electrode substrate 123 (e.g., ultra-thin or flexible regions). Continuous conductive elements may include at least one proximal contact pad 62, at least one interconnect 68, and at least one distal contact 16. The continuous conductor preferably contains no discontinuity or joint between the wire-receiving pad and the distal contact 16. The continuous conductive elements may be comprised of a patterned metal foil (e.g., between 10 and 150 um) using a noble metal (platinum, platinum-iridium, palladium, stainless steel, etc.), and may also be a deposited conductor (e.g., a conductive epoxy, conductive ink) or a patterned conductor (e.g., sputtered metal or electrodeposited). In a preferred embodiment, the continuous conductive elements are flexible, and the electrode therapy contacts 16 are also flexible. In FIG. 15 (left), the lead body 620 contains one or more conductor wires 64 that may be attached to a proximal receiving pad 63 or a medial receiving pad 62.

In another embodiment, continuous conductive elements may enable a thin substrate 123 to be positioned adjacent to the pedicle 58 with electrical stimulation contacts 16 positioned laterally adjacent to dorsal roots 24 and dorsal column 18 in a medically uncompressed manner. FIG. 15 (left), for example, shows wire-receiving pads 62 that enable lead-body conductor wires to be connected to the electrode array 110. The lead body 620 normally contains 1-16 conductors, which are comprised of single-strand or multi-strand conductors approximately 0.002-0.008" in diameter housed within a tubing normally made from silicone or polyurethane. The wires may be composed of a noble metal (e.g., platinum-iridium, SS316LVM), or a metal-to-metal composite with a silver core (e.g., 35NLT-DFT-28% Ag, MP35N-DFT 28% Ag). The conductor wires are typically insulated in a fluoropolymer, such as PTFE, FEP, PFA, or ETFE with an exemplary insulator wall thickness of about 0.001". In one embodiment, the conductors within the lead body 620 are at least partially coiled such as a helix. In another embodiment the conductors inside the lead body 620 are straight. Each conductor generally has individual insulation and an outer tubing that contains all the conductors. The outer tubing may have multiple lumens, such that each lumen has one or more conductors. An additional central inner tubing or a lumen may be present to facilitate insertion of stylus through the lead wire. The proximal end of the lead wire has cylindrical contacts that enable electrical connection with IPG 500.

The medial receiving pads 62 (FIG. 15) preferably are located near the longitudinal axis of the therapy array 110 with continuous conductive elements extending horizontally to a contact positioned laterally in the therapy array 110. The continuous conductive elements may exist within one sub-region of the therapy array 110 or the elements may extend between two sub-regions of different thickness and stiffness. FIG. 15 (right), depicts the receiving pads at the proximal end of the electrode array 110, for receiving wires from the lead body 620. The continuous conductive elements extend from the proximal end of the therapy array 110 to form the contacts at the distal end. The wires may attach to the wire-receiving pads by welding, conductive epoxy, compression bonding, brazing, thermal bonding, cold-welding, soldering or other metal-joining methods. The exposed welds and wires may be molded with silicone, polyurethane, or other encapsulant forming a sub-region of the substrate 123.

Figure 16:
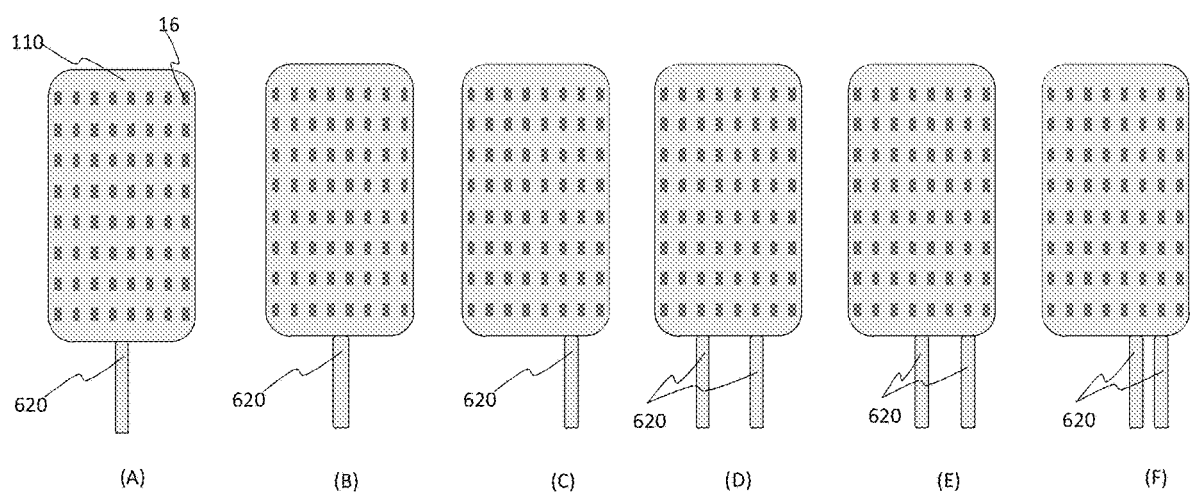
FIG. 16 diagrammatically shows illustrative embodiments of an electrode array with at least one lead exiting the array body from a region of the array that may be on the centerline (A, B, E), off the center line (C, D, E, F) or, if two or more, symmetric about the centerline (D), asymmetric about the centerline (E, F), or on one side of the centerline (F). In addition, the lead may exit the array body at the proximal end (A) or at a location substantially displaced from the proximal end (B).

FIG. 16 shows the lead body connection to the therapy array 110 at one or more lateral positions along the proximal end of the electrode substrate 123 (*a*), (*c*), (*d*), (*e*), (*f*). The lead body 620 may also be positioned at a different longitudinal location other than the proximal longitudinal edge as shown in (*b*).

Electric-field modeling enables a predictive mapping of neural activation of different sensory and motor fibers in the spinal cord 14 and dorsal roots 24. By calculating the propagation of the electric field through the dura mater 34, cerebrospinal fluid 38 (3-4 mm thick), and the grey and white matter of the spinal cord 14, the extracellular potential distributions can be used to compute the (i) the spatial distribution of sensory and motor fiber activation thresholds in the dorsal columns 18, (ii) the threshold of activation of sensory and motor fiber within the dorsal roots 24, (iii) the activation threshold at which the patient would feel paresthesia, (iv) the activation threshold at which the patient would feel discomfort, (v) the distribution of nerve fiber recruitment within the dorsal column 18 at the patient discomfort threshold. Compressive and non-compressive methods of stimulation can be evaluated and validated for quantitative predictive assessment of therapeutic benefit.

Figure 17:
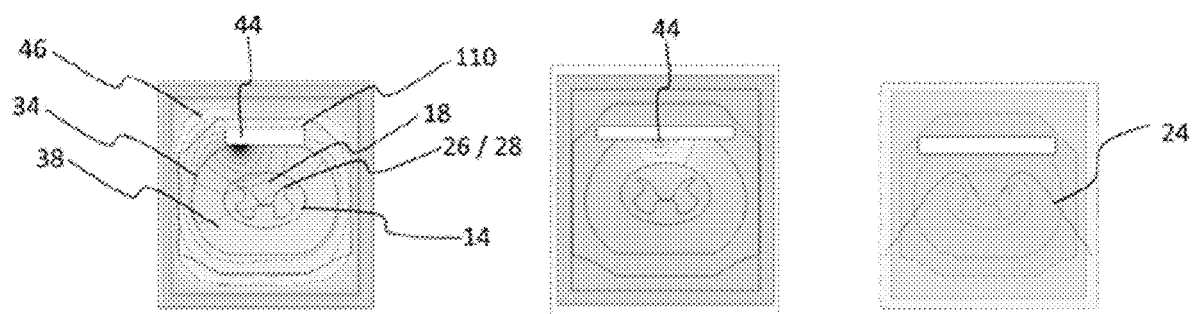
FIG. 17 shows the structures used in the electric field simulation models for compressive, plate-type electrode arrays (thick and smaller paddle (left), thin and wider paddle (middle)) positioned at the anatomical midline and the computed electric field distribution from the simulation stimulation. The figure on the right shows position of the roots in the model which may not be depicted in other images showing the model.

Three-dimensional models of a (i) compressive plate-type, and (ii) non-compressive conformal electrode array 110 were generated to validate various embodiments of the invention. Initially, the model was applied to a compressive plate-type electrode array 110 as shown in FIG. 17, left. The plate-type array 110 flattens the dura mater 34 over an 8 mm lateral span centered at anatomical midline. As shown in the figure, when lateral contacts 16 are activated 44, the electric field distribution 46 propagates to the spinal cord 14. Similarly, the dorsal root 24 activation is computed using a longitudinal distribution of the electric field.

Figure 18:
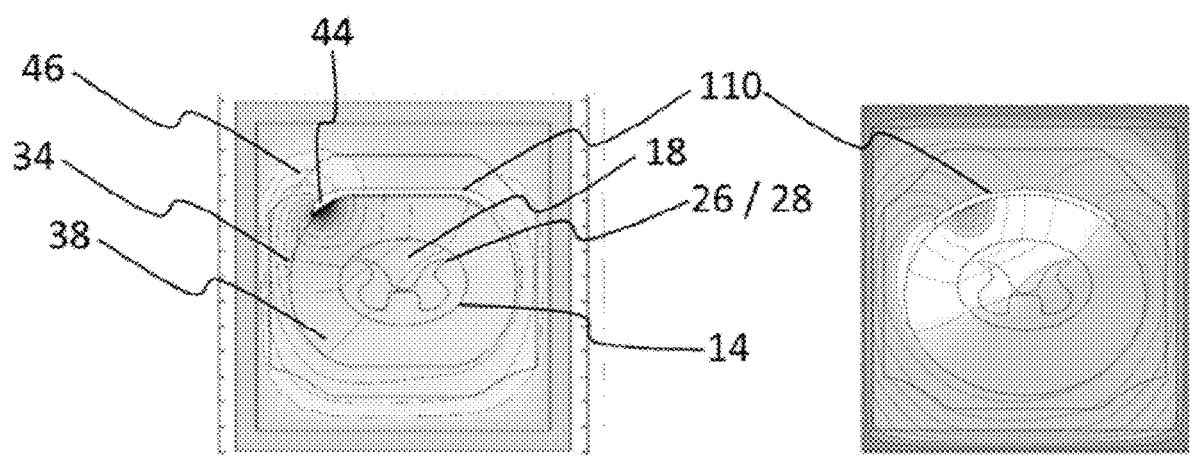
FIG. 18 shows the structures used in the electric field simulation models for a non-compressive and flexible electrode array positioned above the anatomical midline and the computed electric field distribution from the stimulation. Lateral contacts were activated to create the electric field distribution contours.

Non-compressive electrode arrays 110 were also developed having a low-profile, stiffness, and volume geometries that conform to the dura mater 34 as shown in FIG. 18. The electrode arrays 110 are depicted and show (i) safe midline dura mater compression (8 mm span) with no neural tissue compression (left), and (ii) no dura matter compression at midline or laterally. For modeling purposes, the electrode array 110 had eight (8) columns of contacts 16. FIG. 18 depicts the electric field distribution 46 when the electrode array 110 is implanted with contacts 16 adjacent to the lateral extents of the dorsal column 18, dorsal root entry zone 28, and the dorsal roots 24, and when lateral sites are activated 44.

Figure 19:
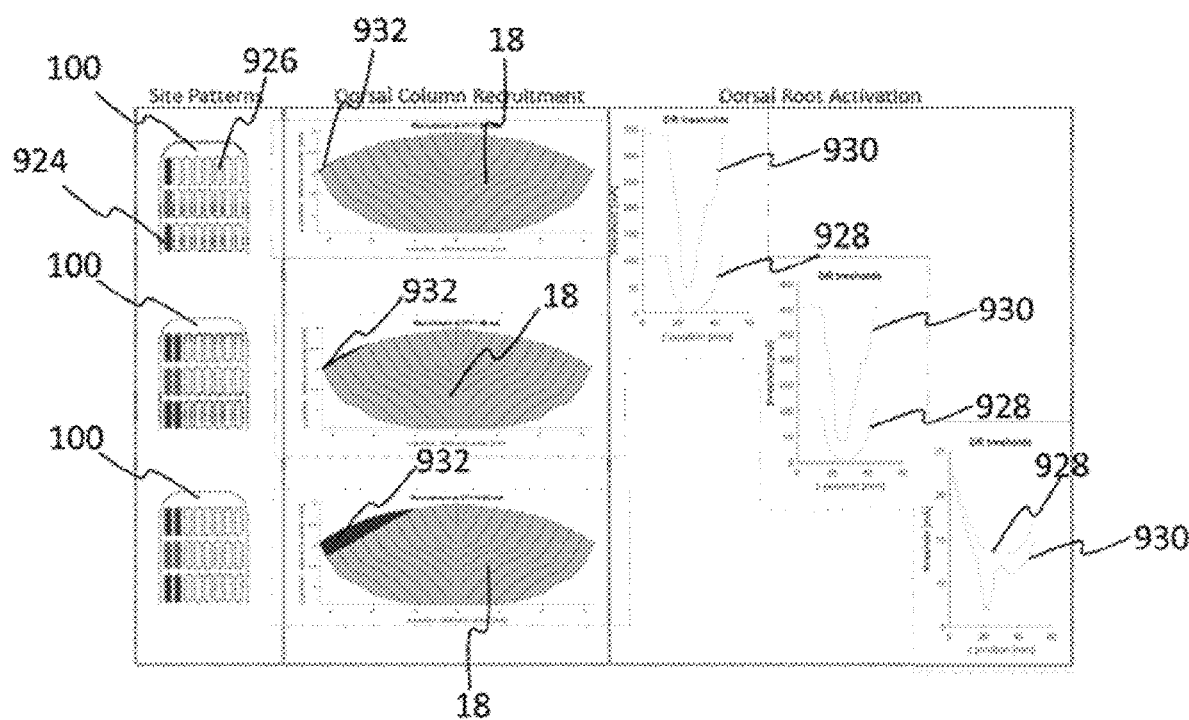
FIG. 19 shows electric field models applied to multiple contacts (left) including top: a vertical tripole, middle: a double vertical tripole, bottom: a double tripole with anodal intensification; the resulting activation of lateral neural tissues of the dorsal column (middle); and the corresponding left and right dorsal root activation (right).

FIG. 19 shows one embodiment of the method for non-compressibly stimulating one or more lateral neural tissues, which activates a subset of the lateral fibers and fasciculi 30 of the dorsal columns 18 corresponding to at least one sub-region of the patient's body. The left column of FIG. 19 shows typical contact 16 configurations (vertical tripole, double-vertical tripole, and anodal-intensification of double-vertical tripole). When these or other patterns of stimulation electrodes 924 are applied using some of the noted non-compressive embodiments, one or more subsets of the lateral dorsal columns 18 are recruited up to the discomfort threshold (middle). The middle column shows the anatomical segmentation of the recruited fasciculi 932 of the dorsal column 18, which correspond to the sub-region of the patient's body (see mapping in FIG. 20). The right column shows the left and right dorsal root activation thresholds 928, 930 versus vertical offset between the nerve root 24 and the electrode array 110. The lowest point of the dorsal root curve indicates the minimum threshold at which the dorsal root 24 may become activated. Similarly, the paresthesia threshold, dorsal column threshold, and discomfort thresholds can be computed from the dorsal column recruitment maps. The discomfort thresholds of dorsal column fiber recruitment with the first and second site patterns are 7.96 mA while the third contact pattern is 14.65 mA. Similarly, the dorsal root activation with the first and second contact pattern have a dorsal root threshold of 5.7 mA, and the third contact pattern 10.5 mA activation. Activation of lateral fibers of the dorsal column 18 is demonstrated with accompanying dorsal root activation (first, second site patterns) and with no dorsal root activation (bottom site pattern.

FIG. 19 demonstrates a method for stimulating one or more lateral neural tissues, selecting one or more contacts 16 in the implanted non-compressive electrode array 110, and applying a stimulation pattern to those sites. This method activates a subset of the lateral fibers and fasciculi 30 of the dorsal columns 18 corresponding to at least one sub-region of the patient's body. The left column of FIG. 19 shows typical contact 16 configurations (vertical tripole, double-vertical tripole, and anodal-intensification of double-vertical tripole). When these or other patterns of stimulation electrodes 924 are applied using the non-compressive embodiments, one or more subsets of the lateral dorsal columns 18 are recruited up to the discomfort threshold (middle).

Figure 20:
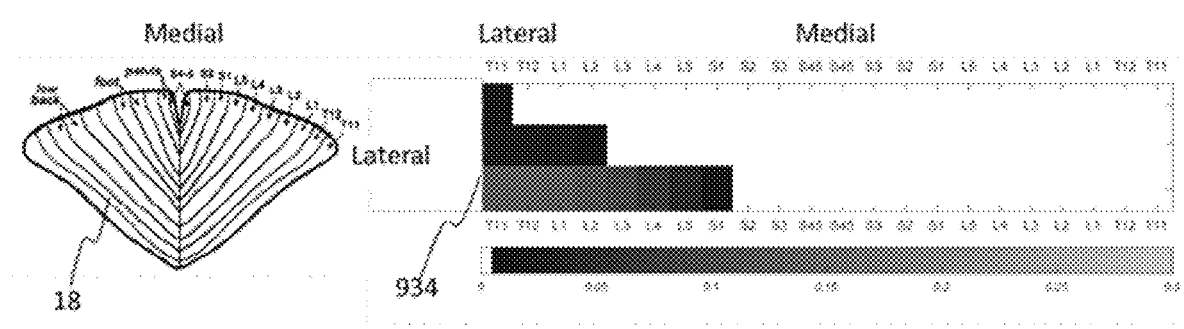
FIG. 20 shows the position of the dorsal column fasciculi segments and the corresponding dermatome mapping at the T10 vertebral level (left). The lateral dorsal columns which were activated in FIG. 19 correspond to the depicted sub-regions of the patient's body (right).

The middle column shows the anatomical segmentation of the recruited fasciculi 932 of the dorsal column 18 that correspond to the sub-region of the patient's body (see mapping in FIG. 20). The right column shows the left and right dorsal root activation thresholds 928, 930 versus vertical offset between the nerve root 24 and the electrode array 110. The lowest point of the dorsal root curve indicates the minimum threshold at which the dorsal root 24 may become activated. Similarly, the paresthesia threshold, dorsal column threshold, and discomfort thresholds can be computed from the dorsal column recruitment maps. The discomfort thresholds of dorsal column 18 recruitment with the first and second site patterns are 7.96 mA while the third contact pattern is 14.65 mA. Similarly, the dorsal root activation with the first and second contact pattern have a dorsal root threshold of 5.7 mA, and the third contact pattern 10.5 mA activation. Activation of lateral fibers of the dorsal column 18 is demonstrated with accompanying dorsal root activation (first, second site patterns) and with no dorsal root activation (bottom site pattern).

When the activated fibers 932 within each dorsal column activation map of FIG. 19 are segmented into dermatomal fasciculi maps 934, the corresponding sub-regions of the patient's body (e.g., dermatomes) where the patient will feel therapy can be mapped. FIG. 20 (left) shows a cross-section of the T10 vertebral level dorsal column 18 and the position of the sensory fibers of the corresponding dermatome (see FIG. 8). FIG. 20 (right) shows the recruitment of each dorsal column segment (x-axis) that are activated by the three site patterns (each vertical row). The method of stimulation can selectively activate the lateral dorsal columns 18 without the dorsal roots 24.

Figure 21:
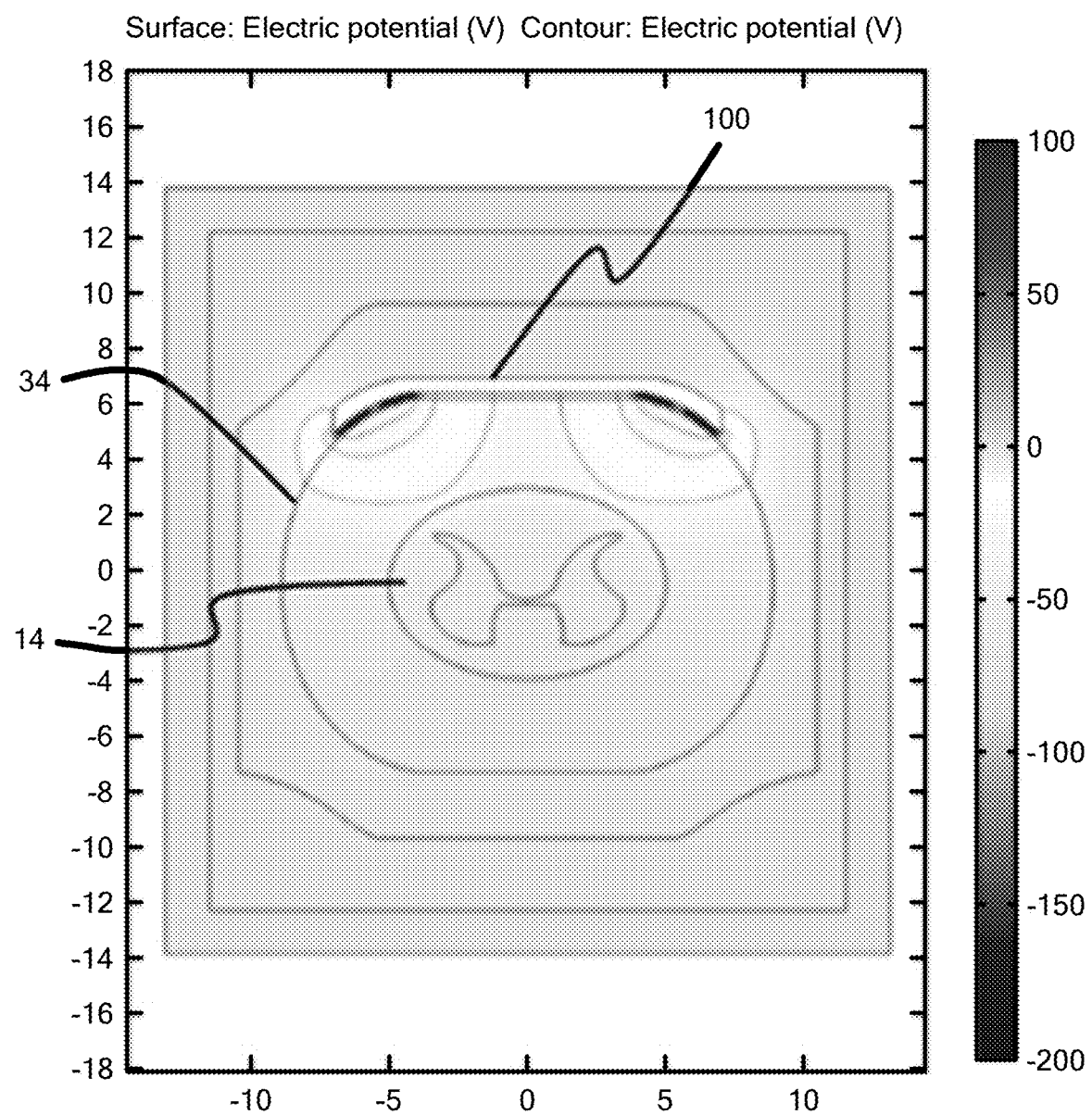
FIG. 21 shows one incarnation of the electric field model applied to a non-compressive, flexible electrode array positioned above the dura at the anatomical midline and the electric field distribution from this computation. Lateral contacts were activated on both sides of the spinal cord to create a bilateral electric field distribution.

In another embodiment, the method stimulates dorsal roots 24 and dorsal columns 18 adjacent to the pedicle 58 on both sides of the patient's body, selects one or more contacts 16 in the implanted and non-compressive electrode array 110, and applies a stimulation pattern to those contacts 16 to activate a subset of the lateral fibers or fasciculi of the dorsal columns 18 that correspond to at least one sub-region on both sides of the patient's body (e.g., bi-laterally: upper extremity, low-back, feet, headache, bladder, sphincter). Referring again to FIG. 14 (right), which shows two non-compressive electrode arrays 100 positioned adjacent to the pedicle 58 in a medically uncompressed manner, with stimulation contacts 924 positioned to stimulate the lateral dorsal columns 18, the dorsal roots 24, and the dorsal root entry zones 28. The electric field distribution of activated nerve fibers can be computed as shown in FIG. 21.

In one embodiment, the method of applying stimulation from the non-compressive electrode array 110 to a subset of one or more of the lateral dorsal columns 18 to provide therapy to at least one sub-region on both-sides of the patient's body. In another embodiment, the method of non-compressive stimulation is applied to at least a subset of one or more dorsal roots 24 or the dorsal root entry zones 28 to provide therapy to one or more associated sub-regions on both sides of the patient's body. In yet another embodiment, the method of non-compressive stimulation is applied to a combination of dorsal columns 18 and dorsal roots 24 for providing therapy on one or more associated sub-regions on both sides of the patient's body. In still another embodiment, the method of non-compressive stimulation is applied to a combination of lateral fibers of the dorsal column 18 and dorsal roots 24 on both sides of the patient's anatomical midline are stimulated to provide therapy one or more associated sub-regions on both sides of the patient's body.

Figure 22:
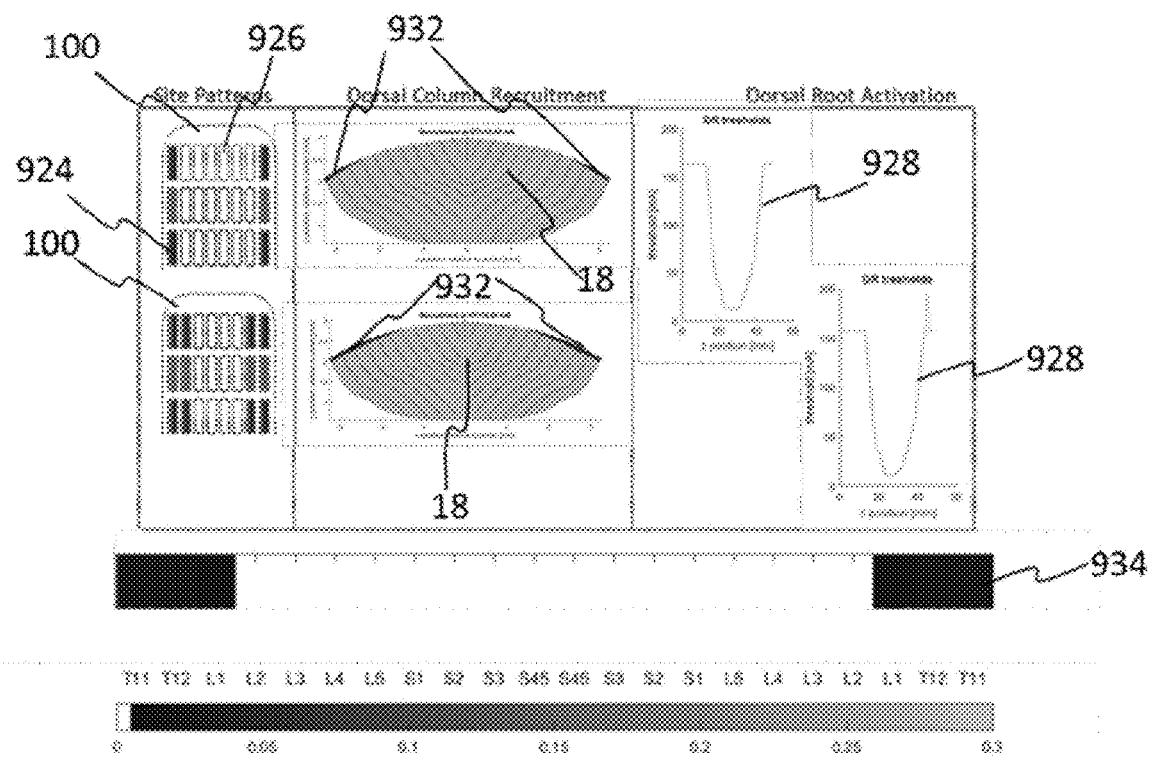
FIG. 22 shows the results of electric field models applied using two contacts (left, row 1 and row 2). The resulting activation of lateral neural tissues on both sides of the dorsal column (middle) and the corresponding left and right dorsal root activation (right).

The method of applying stimulation to lateral neural tissues 17 adjacent the pedicle 58 on both sides of the spinal cord 14, selecting one or more contacts 16 in each the implanted, noncompressive electrode array 110, and applying a stimulation pattern to those contacts 16 is demonstrated in FIG. 22. This method activates one or more lateral fibers and fasciculi of the dorsal columns 18 that correspond to at least one sub-region of the patient's body on both sides of the body. The left column of FIG. 22 shows typical contact configurations 924 (vertical tripole, double-vertical tripole). When these or other patterns are applied using illustrative embodiments, one or more subsets of the lateral dorsal columns 18 are recruited 932 up to the discomfort threshold (middle).

The middle column shows the anatomical segmentation of the fasciculi of the dorsal column 18 that correspond to the sub-region of the patient's body (see mapping in FIG. 20). The right column shows the left and right dorsal root 24 activation thresholds versus vertical offset between the nerve root 24 and the electrode array 110. The discomfort thresholds of dorsal column recruitment with the first contact pattern is 14.6 mA, while the second pattern is 15.5 mA. Similarly, the dorsal root 24 activation with the first contact pattern is 10.4 mA, and the second site pattern 11.0 mA activation. Activation of lateral fibers on both sides of the dorsal column 18 is demonstrated with accompanying dorsal root activation.

Figure 24:
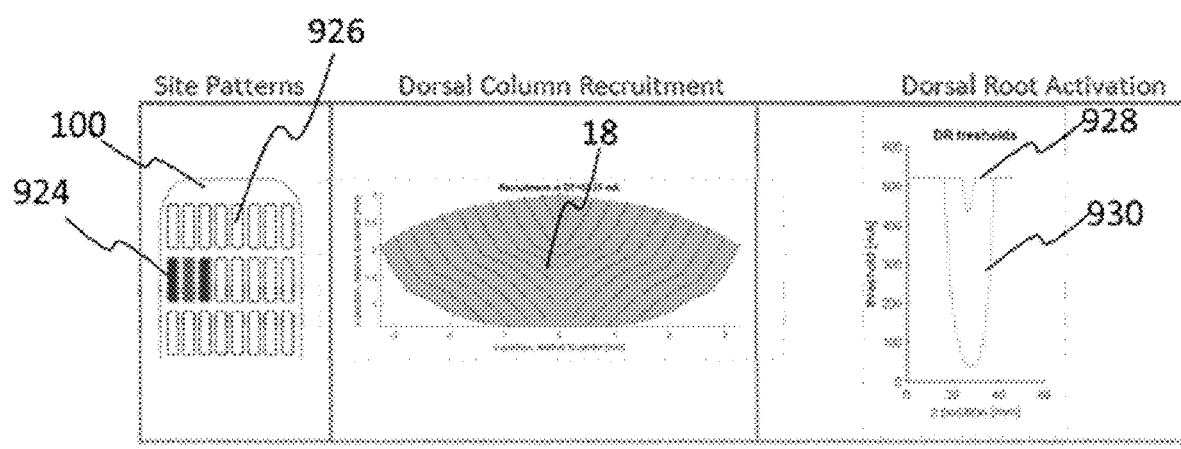
FIG. 24 shows the results of electric field models applied using a transverse tripole configuration. The transverse tri-pole results in no activation of the dorsal columns (middle) but and a significantly lower dorsal root activation threshold (right).

In another embodiment, the method of non-compressive stimulation may be utilized to selectively activate a dorsal root 24 without activation of the dorsal column 18. The method of implanting the non-compressive electrode array 110 adjacent to lateral neural tissues 17, selecting one or more contacts 16 in the electrode array 110, and applying a stimulation pattern 924 to those contacts 16 is demonstrated in FIG. 24. This method provides no activation of the dorsal columns 18 but a substantially lower dorsal root 24 activation threshold that corresponds to at least one sub-region of the patient's body. The left column of FIG. 24 shows the transverse tripole configuration while the center column illustrates a discomfort threshold of 52 mA with no portions of the dorsal columns 18 recruited. The right figures show the left dorsal root 24 having a recruitment threshold of less than 25 mA, 930.

Figure 23:
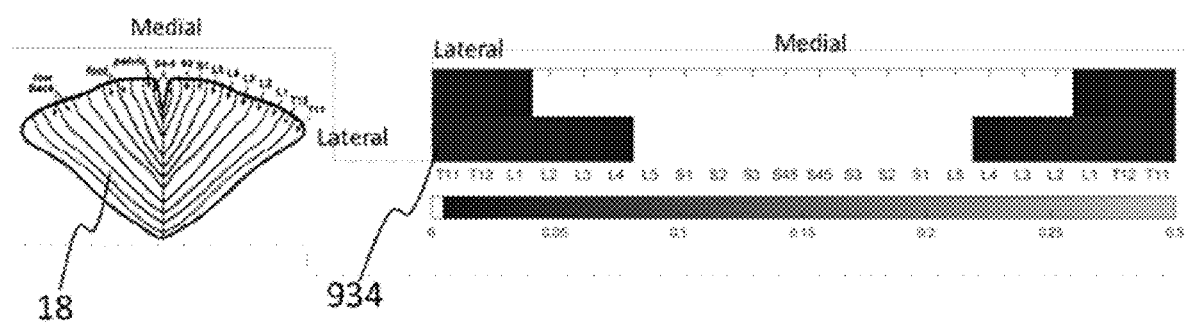
FIG. 23 shows the position of the dorsal column fasciculi segments and the corresponding dermatome mapping at the T10 vertebral level (left). The lateral dorsal columns which are shown to be activated bi-laterally in FIG. 22 correspond to the depicted sub-regions on both sides of the patient's body (right).

FIG. 23 (left) shows a cross-section of the T10 vertebral level dorsal column 18 and the position of the sensory fibers of the corresponding dermatome (see FIG. 8). FIG. 23 (right) shows the recruitment of each dorsal column segment (x-axis) that are activated by the two contact patterns 924 (each row). The non-compressive method of stimulation can substantially activate the lateral dorsal columns 932 and nerve roots 928 corresponding to one or more sub-regions on both sides of the patient's body with or without root activation.

One or more columns of contacts 16 provide more opportunities to localize therapy to one dorsal column 18 associated with a sub-region of the patient's body. Conceptually, sub-perception or paresthesia based pain relief could be provided to sub-regions of the patient's body without delivering therapy to adjacent or intervening sub-regions of the patient's body, but in practice is dominated by both the number of contacts 16 per unit area and the CSF thickness between the sites and fibers.

Reiterating above, various embodiments involve a non-compressive electrode array 110 (i.e., an array 110 that operates in a medically uncompressed manner) that conforms to the dura mater 34 after implantation, and which has a substrate 123 with sub-regions of prescribed thicknesses that may be positioned adjacent to the dorsal roots 24 and pedicle 58 in a medically uncompressed manner. Various embodiments involve multi-contact therapy arrays 110 with contacts 16 arranged in low or high-density spatial configurations. For example, the therapy array 110 may contain 16, 32, or 64 contacts 16 for extradural implantation. In one embodiment (FIG. 25 left), the electrode array 110 has about 8 rows and 8 columns with lateral most columns positioned to stimulate the roots. Some arrays 110 can have more rows and columns, such as up to 20 each. In another embodiment (FIG. 25, middle), lateral most columns of the electrode array 110 have more contacts 16 than medially placed columns of contacts 16. In another embodiment (FIG. 25, right), double-pairs of lateral most columns of the electrode array 110 has more contacts than medially placed columns of contacts 16. Those skilled in the art will recognized that before joining the spinal cord 14 via the dorsal root entry zone 28, the dorsal root 24 splits longitudinally into multiple rootlets and rootlets enter the dorsal column 18.

Figure 25:
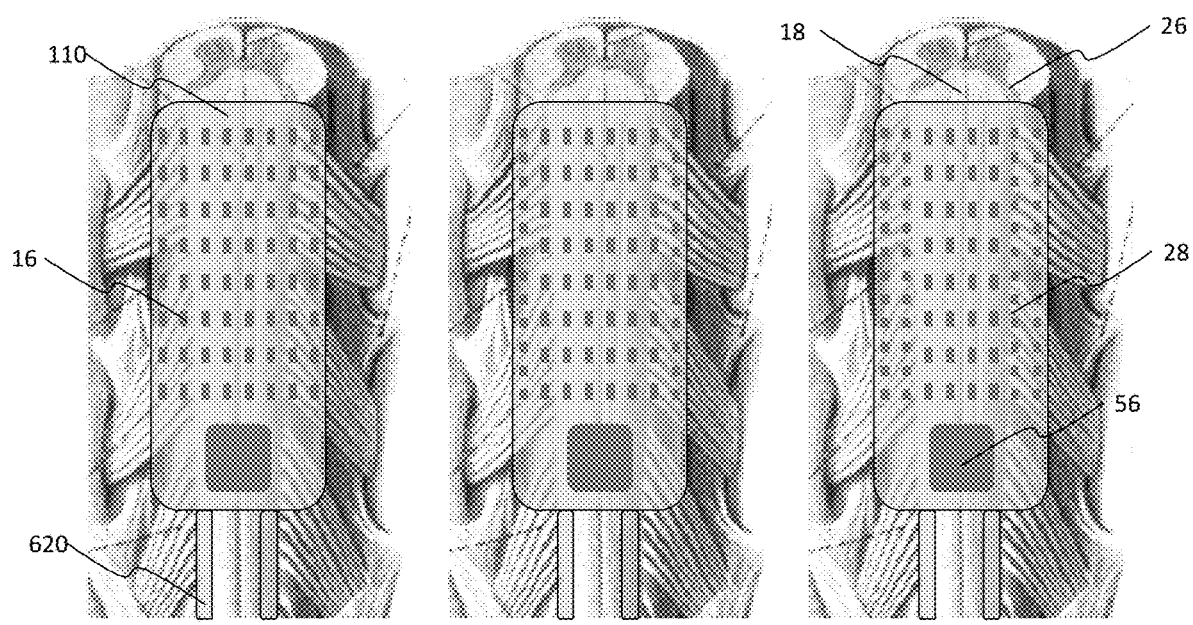
FIG. 25 diagrammatically shows three (3) embodiments of non-compressive electrode arrays (i.e., electrode arrays that do not impart significant compression as discussed below) overlaid to show the approximate interactions between the contacts and the subdural neuronal tissues to be targeted for therapy. Electrode arrays may have an equal number of rows for all columns (left), may have an increased number of rows on the lateral most columns (center) to increase resolution for stimulation of the dorsal roots and dorsal root entry zone, or may have an increased number of rows on many of the lateral columns (right).

FIG. 25 shows one embodiment that has more rows of contacts 16 on one or more lateral columns of the electrode array 110 than the middle columns. This arrangement is intended to provide selective stimulation to lateral fibers. The increase in the number of rows along the lateral column enables selective stimulation of a subset of nerve rootlets without stimulating another subset of nerve rootlets. In this embodiment, the electrode array 110 is positioned epidurally, though the figure depicts the subdural perspective so that the neural rootlet targets are displayed.

Figure 26:
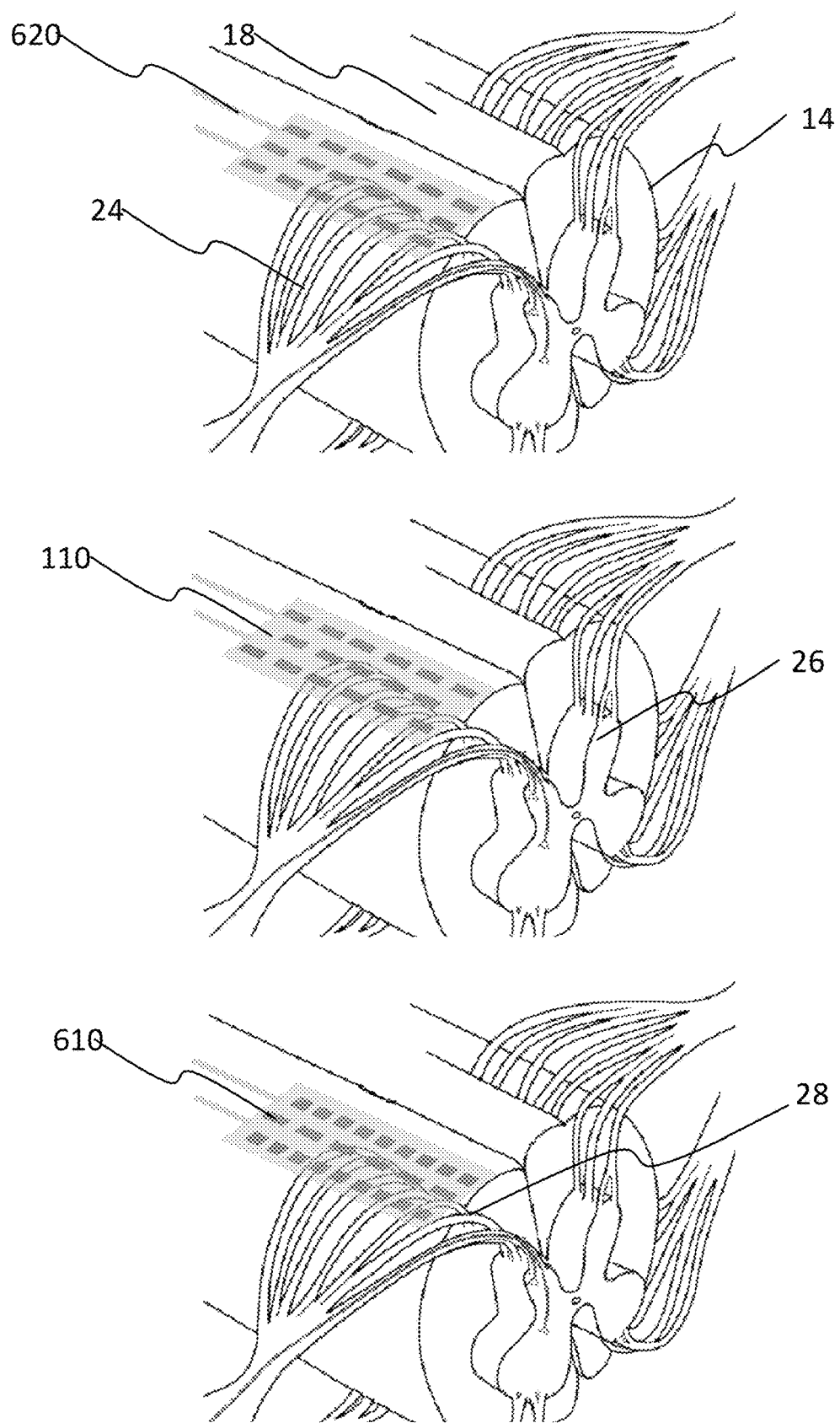
FIG. 26 diagrammatically shows three (3) embodiments of non-compressive electrode arrays overlaid to show the approximate interactions between contacts and the subdural neuronal tissues of the dorsal roots or dorsal root entry zone as well as the dorsal column. The three embodiments include symmetrically spaced electrode arrays with uniform therapy contact density (top), asymmetrically spaced therapy contact with uniform therapy contact density (center), and asymmetrically spaced therapy contact with non-uniform therapy contact density (bottom).

In another embodiment, an electrode array 110 may contain 16, 32, or 64 contacts 16 positioned on the substrate 123. The non-compressive electrode array 110 may contain contacts 16 arranged in a two-dimensional configuration. In one embodiment, the contacts 16 have one or more columns with fewer or more sites in the adjacent column. In another embodiment, the contact rows or columns may be substantially adjacent (FIG. 26, top). In another embodiment, the rows or columns of contacts 16 may be offset compared to one or more adjacent rows or columns (FIG. 26, middle). Alternatively, the contacts 16 may have one or more rows that have fewer or more contacts 16 than an adjacent row (FIG. 26, bottom).

For these embodiments, the electrode array 110 has a sufficient width to provide contacts 16 extending from the left root and pedicle 58 to the right dorsal root 24 and pedicle 58, as well as all intervening dorsal columns 18. In another embodiment, however, the electrode array 110 has a sufficient width to provide stimulation extending from the left or right pedicle 58 up to the anatomical midline.

Figure 27:
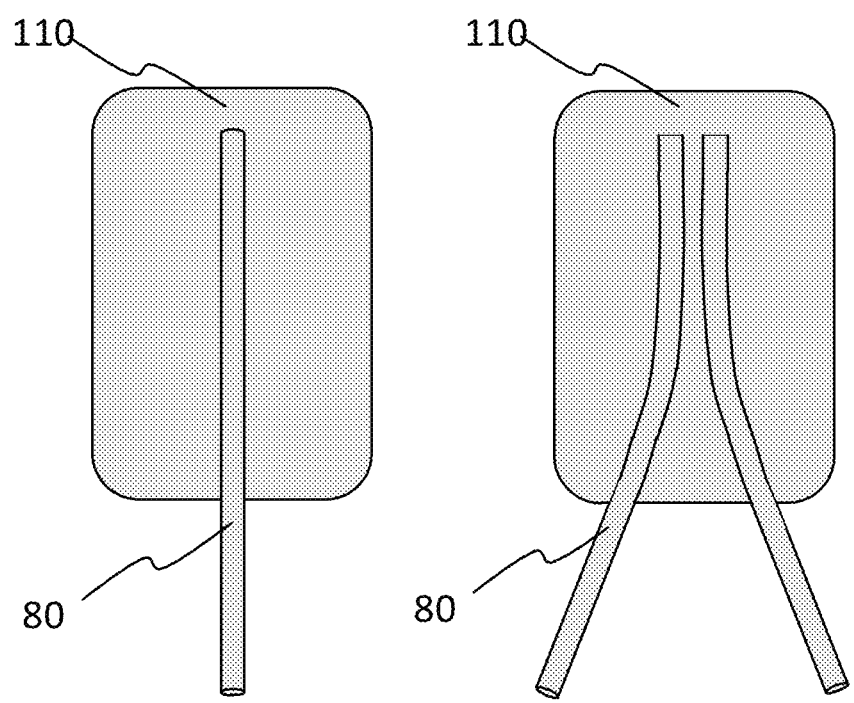
FIG. 27 shows two (2) embodiments of electrode arrays with channels or guides allowing for a stylus or guide wire to be inserted to aid in advancement and steering of the electrode array within the epidural space. Left: a single stylus positioned at midline may be used. Right: multiple styluses may be used and may have features which aid in steering including curves or angled entry zones.

FIG. 27 shows additional therapy array features for inserting one or more guide wires or styluses 80, which stiffens the substrate 123 during advancement and allow for steering and placement. After removal of the guide wire, the substrate stiffness is substantially more flexible to conform to the spinal cord 14 and couple more effectively.

As depicted in FIG. 2, the therapy array 110 may be electrically connected to the IPG 500 through a lead wire having multiple electrical conductors. This system also may have a gating or multiplexing unit positioned between the IPG 500 and the electrode array 110, in which the total number of conductors in the lead body 620 are fewer than the number of independently accessible contacts 16. Among other places, gating or multiplexing unit can be positioned within the electrode substrate body.

The therapy array 110 also may be used for recording spinal cord signals (c-fiber, a-alpha, a-beta, a-delta fibers), nerve root signals, or other physiological signals. The therapy sites also may provide an acoustic our ultrasonic pressure wave to provide stimulation therapy to the dorsal columns 18, dorsal roots 24, and other relevant spinal neural features.

Figure 28:
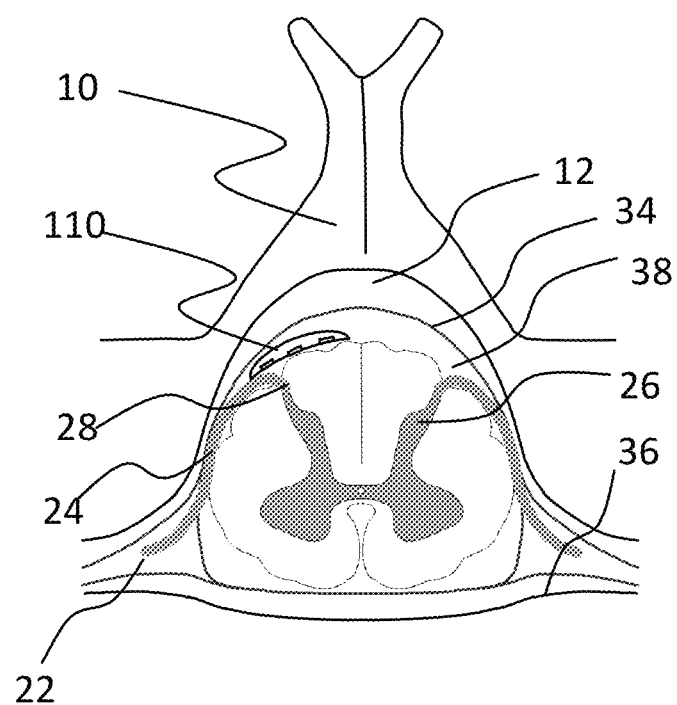
FIG. 28 diagrammatically shows one example of a non-compressive electrode array positioned to target the dorsal root entry zone and lateral dorsal column fibers with the substrate positioned sub-dura, where the therapy array is implanted in a medically uncompressed manner relative to the spinal cord, and spinal rootlets within the dura in the illustrative embodiments.

Improved focus of therapy to discrete dorsal columns 18, dorsal roots 24, and fasciculi may be possible using subdural contacts 16 coupled directly to the spinal cord 14. FIG. 28 shows an embodiment of the invention that stimulates the spinal cord 14 by implanting the electrode array 110 within the subarachnoid 38 space beneath the dura mater 34 in a medically uncompressed manner, and applies a stimulation pattern to one or more contacts 16 on the electrode array 110. This should provide therapy to a specific sub-region of a patient's body (e.g., pain relief, bladder function, motor function, headaches, and other therapies).

As known by those in the art, the epidural space 12 at the anatomical midline can be very thin (e.g., less than about 2 mm) in the cervical spine. At the cervical spinal level for example, the epidural space 12 is wider in the lateral extent, but thinner in the dorsal direction. Standard of care would screen patients using MRI and preclude using prior-art electrodes in such low-volume epidural spaces 12.

Another embodiment relates to method of stimulating one or more neural tissues of the spinal cord 14 at any longitudinal vertebral level (cervical, thoracic, lumbar, sacral) at any medial-lateral dorsal columns 18, dorsal root entry zones 28, dorsal horns, or dorsal roots 24, and implanting an electrode substrate 123 in any region. Importantly, this embodiment stimulates in a medically uncompressed manner—not compressing the dura mater 34 by more than about 1 mm—selects one or more contacts 16, and delivers one or more stimulation pulse patterns to the sites to provide therapy preferentially to one or more sub-regions of the patient's body.

Figure 29:
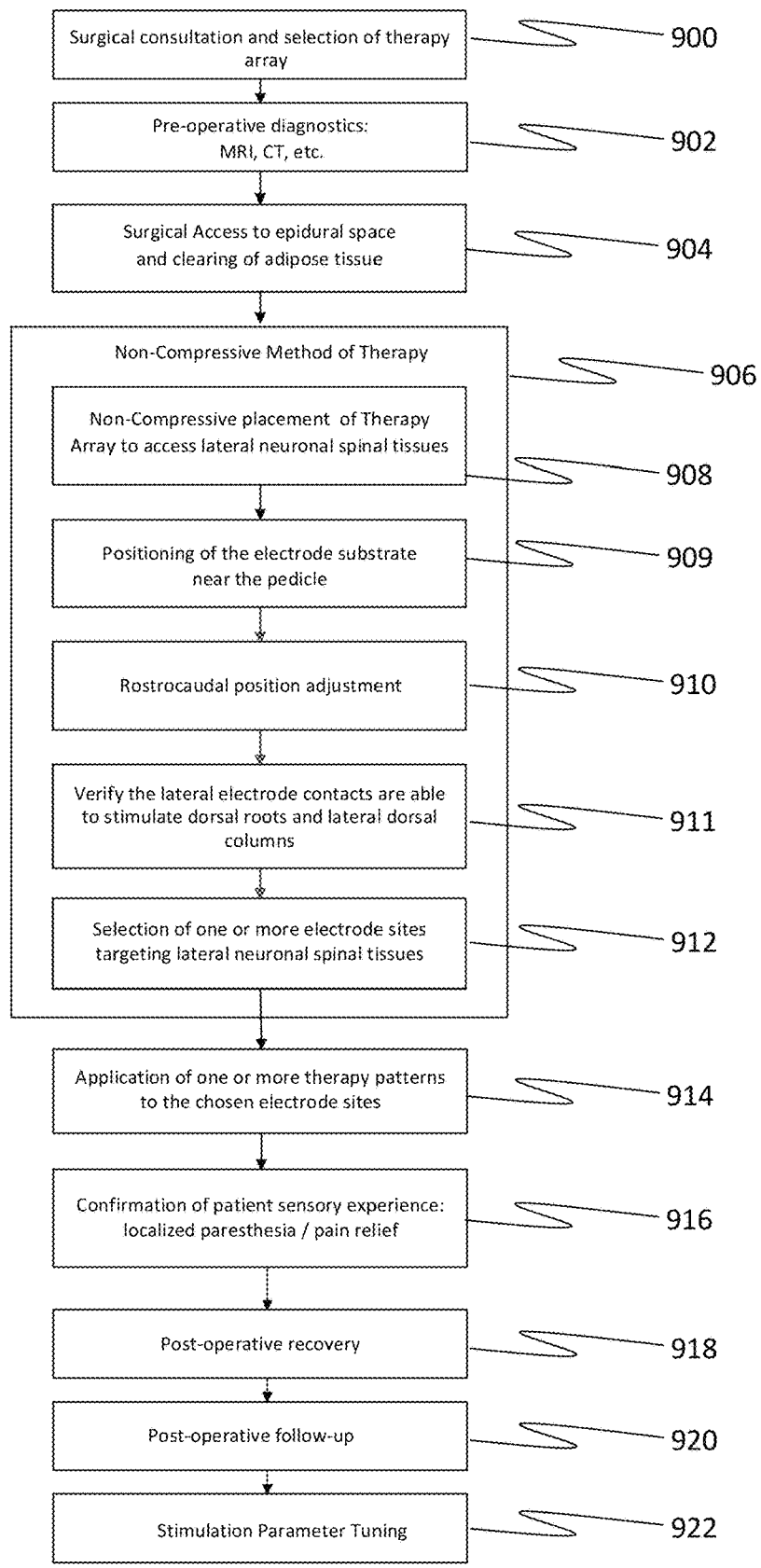
FIG. 29 is a flow-chart of a method of assisting a person in accordance with illustrative embodiments.

FIG. 29 shows a flow-chart of the method stimulating a spinal tissue by implanting an electrode array 110 with one or more conformal sub-regions with lateral substrate edges adjacent to the pedicle 58 in a medically uncompressed manner. It should be noted that this process is a simplified version of a complex process and thus, may omit various steps. Moreover, some steps may be completed in a different order than that shown, or at the same times as other steps.

As shown by this flow-chart, illustrative embodiments overcome the surgical and anatomical limitations by providing a method for therapeutic stimulation of neural tissues to alleviate pain or other physiological deficit within a sub-region of a patient's body. It also should be noted that although the flow-chart describes stimulation for chronic pain, the method may also be used to treat other issues, such as urinary tract disfunction, motor function, or cardiac dysfunction.

The process begins when a patient undergoes surgical consultation 900 for implantation of a spinal cord stimulator. Candidate subjects may have a pre-operative MRI, ultrasound, x-ray or computed tomography scan 902 to perform surgical planning and risk analysis. In particular, the volume, shape, and features of the epidural space 12 are examined at the relevant spinal vertebral level required to position the electrode for optimal therapy. Areas of obstructions or constrictions may pose a surgical risk, which may prevent the use of the therapy array 110. For example, the lateral regions of the epidural space 12 near the pedicle 58 adjacent to the dorsal roots 24 may be a constricted. Assuming all goes well in the assessment, the patient will be cleared for a surgical implantation of the therapy array 110 and the IPG 500.

A standard of care surgical procedure begins with an initial incision and a subperiosteal dissection down to the lamina near the vertebral segment of interest. The electrode array 110 is surgically placed by removing part of the vertebral segment (laminotomy/laminectomy) at the cervical, thoracic, lumbar, or sacral regions of the spinal cord 14. The ligamentum flavum is then removed 904 and vertebral foramen 13/36 is exposed 906. Epidural fat and other tissue is cleared from the epidural space 12, taking care to avoid pressure on the spinal cord 14. The electrode array 110 is inserted within the epidural space 12 in a manner to avoid medical compression of the dorsal roots 24 or spinal cord 908.

The method of stimulation in a medically uncompressed manner begins by positioning the electrode array 110 so that one edge of its substrate 123 is adjacent to the pedicle 909 in the epidural space 12 (the sub-dural embodiment is not depicted in the flow-chart). The rostro caudal position may be optimized by advancing the electrode array 110 longitudinally 910. The lateral positioning of the conformal array 110 enables electrode stimulation contacts 16 to be located adjacent to dorsal roots 24, dorsal root entry zone 28, and lateral fibers for optimal stimulation delivery. The electrode contacts 16 may also be located across the span of the dorsal columns 18. Lateral positioning may be verified intraoperatively 911 using surgical assessment, electrophysiological assessment, or radiologic imaging methods (e.g., c-arm).

Frequently, the electrode array 110 may be temporarily removed to clear adipose tissue or other obstructions to facilitate positioning within the spinal cord 14. Some embodiments may engage in an intraoperative trialing session in which the patient is woken up and asked to verify the perception of stimulation as the position of the lead is adjusted and different contacts 16 are stimulated. In the preferred embodiment, however, the patient should not require an intraoperative trialing session due to the substantially improved coupling from the substrate mechanical properties, and the provision of contacts 16 near the dorsal roots 24, dorsal root entry zone 28, and dorsal columns 18.

In an intraoperative or post-operative setting, the electrical stimulation contacts 16 or combinations of contacts 16 are selected 912 and one or more stimulation waveforms (tonic, sub-perception, and/or burst) are applied to the selected contacts 914. If applicable, verification of parasthesie in the desired dermatomes by the patient is confirmed 916. If pain relief is not achieved, other stimulation electrodes may be activated. If stimulation cannot provide the desired parasthesie, surgical steps may be necessary to reposition the lead within the vertebral canal. In a preferred embodiment, no lead revisions would be necessary as illustrative embodiments provide for electrodes between the left pedicle 58 across all the dorsal columns 18 to the right pedicle 58. Illustrative embodiments cover one or more longitudinal vertebral levels. Accordingly, the preferred embodiment does not have any additional anatomical space to cover.

After the lead bodies are tunneled beneath the skin to the pocket where the IPG 500 is implanted, the operation is complete. The patient is taken to post-operative recovery 918. After the surgery, one or more post-operative follow-ups 920 are performed to select stimulation contacts 16 and provide the patient with different waveforms or stimulation programs for providing therapy. The process may conclude at a simulation parameter tuning 922.

Although the above discussion discloses various exemplary embodiments of the invention, it should be apparent that those skilled in the art can make various modifications that will achieve some of the advantages of the invention without departing from the true scope of the invention.

What is claimed is:

1. A method of assisting a person having spinal cord neural tissue including a plurality of ascending dorsal column fibers and dorsal roots protected by a dura mater and cerebrospinal fluid, the surrounding tissue forming an epidural space, the person also having at least two pedicles and a vertebral foramen, the method comprising:

providing a flexible electrode array having a substrate supporting one or more continuous conductive elements, each of the continuous conductive elements formed by a stimulation contact, a wire-receiving proximal contact, and an interconnect between the stimulation contact and the wire-receiving proximal contact, the continuous conductive element formed having no joints between (1) the interconnect and the wire-receiving proximal contact, and (2) the interconnect and the stimulation contact, the stimulation contact configured to stimulate one or more of at least a portion of the spinal cord neural tissue and a dorsal root and/or rootlet, at least one of the plurality of stimulation contacts configured to be independently stimulated relative to the other contacts; and implanting the flexible therapy array in the epidural space where a first portion of the array is positioned adjacent to at least one pedicle so that stimulation contacts are adjacent to at least one dorsal root laterally within the vertebral foramen at one or more vertebral levels in a medically uncompressed manner relative to at least the dorsal root after implanting, the substrate of the flexible therapy array conforming to the dura mater after said implanting, the substrate having a first region including the continuous conductive element, the first region having a first thickness of between 0.1 mm and 1.5 mm, the continuous conductive element having a thickness of between 10 um and 150 um.

2. The method as defined by claim 1 wherein the vertebral foramen comprises a normal vertebral foramen.

3. The method as defined by claim 1 wherein implanting comprises implanting the flexible array adjacent to at least one of the dorsal column fibers so that at least one stimulation contact is adjacent to the at least one dorsal column fiber.

4. The method as defined by claim 1 wherein each dorsal root has a dorsal root entry zone, wherein implanting comprises implanting the flexible array so that at least one stimulation contact is adjacent to at least one of the dorsal root entry zones.

5. The method as defined by claim 1 further comprising actuating the therapy array after said implanting to stimulate at least one portion of the dorsal column fibers.

6. The method as defined by claim 1 further comprising actuating the therapy array after said implanting to stimulate the dorsal root.

7. The method as defined by claim 1 wherein the dorsal column fibers includes a first fasciculus and a plurality of additional fasciculi, at least one the therapy array stimulation contact being adjacent to the first fasciculus and the dorsal root after said implanting.

8. The method as defined by claim 7 further comprising actuating the therapy array to stimulate the first fasciculus without stimulating the dorsal root.

9. The method as defined by claim 7 further comprising actuating the therapy array to stimulate the first fasciculus and the dorsal root at the same time, or actuating the therapy array to stimulate the dorsal root without stimulating the one or more fasciculi.

10. The method as defined by claim 1 wherein the substrate of the therapy array comprises silicone and/or polyurethane.

11. The method as defined by claim 1 wherein implanting comprises bilaterally implanting at least the flexible therapy array adjacent to at least one pedicle in the epidural space both medially and laterally.

12. The method as defined by claim 1 wherein the two pedicles includes a right pedicle and a left pedicle, the flexible therapy array spanning substantially from at least the left pedicle to at least the right pedicle within the epidural space after said implanting.

13. The method as defined by claim 1 wherein the plurality of stimulation contacts forms an array of stimulation contacts, the array having at least four rows and at least four columns, the array having no more than 20 rows and 20 columns.

14. The method as defined by claim 1, wherein the flexible electrode array includes a plurality of continuous conductive elements defining a plurality of stimulation contacts, the plurality of stimulation contacts positioned in the substrate to stimulate a plurality of dorsal rootlets extending from a common dorsal root.

15. The method as defined by claim 1 wherein the flexible substrate is configured to be curved on at least two parallel or perpendicular axes.

16. The method as defined by claim 1 wherein the person has cerebrospinal fluid, further wherein medically uncompressed implantation is configured not to compress the dura mater and/or cerebrospinal fluid more than 1.2 mm after said implanting to mitigate abnormal dorsal root activation.

17. A method assisting a person having spinal cord neural tissue with a dorsal column, the person also having a plurality of dorsal root entry zones, an epidural space, and dura mater, the person also having a normal vertebral foramen and a plurality of pedicles, the method comprising:

providing a flexible therapy array having a substrate supporting one or more continuous conductive elements, each of the conductive elements including a stimulation contact, a wire-receiving proximal contact, and an interconnect between the stimulation contact and the wire-receiving proximal contact, the stimulation contact configured to stimulate spinal cord neural tissue and/or dorsal roots, the continuous conductive element formed such that there are no joints connecting (1) the interconnect to the wire-receiving proximal contact, and (2) the interconnect to the stimulation contact, at least one of the plurality of stimulation contacts configured to be independently stimulated relative to the other stimulation contacts, the substrate configured to be flexible and further having a prescribed thickness;

implanting the flexible therapy array laterally in the epidural space adjacent to the pedicle with a stimulation contact adjacent to one or both of the dorsal column and the dorsal root entry zone of a first dorsal root, the flexible therapy array also being within the normal vertebral foramen at one or more vertebral levels, the substrate of the flexible therapy array configured to be conformable to the dura mater after said implanting, the substrate having a prescribed thickness of between 0.1 mm and 1.2 mm to implant adjacent to the pedicle within the epidural space, the continuous conductive element accounting for between 10 um and 150 um of the prescribed thickness.

18. The method as defined by claim 17 further comprising actuating the therapy array after said implanting to stimulate at least one portion of the dorsal column.

19. The method as defined by claim 17 further comprising actuating the therapy array after said implanting to stimulate the first dorsal root or the dorsal root entry zone of the first dorsal root.

20. The method as defined by claim 17 wherein the dorsal column includes a first fasciculus and a plurality of additional fasciculi, the therapy array being adjacent to the first fasciculus and the dorsal root entry zone after said implanting.

21. The method as defined by claim 20 further comprising actuating the therapy array to stimulate the first fasciculus without stimulating the first dorsal root.

22. The method as defined by claim 20 further comprising actuating the therapy array to stimulate the first fasciculus and the first dorsal root at the same time, or actuating the therapy array to stimulate the first dorsal root without stimulating the first fasciculus.

23. The method as defined by claim 17 wherein the substrate of the therapy array comprises silicone.

24. The method as defined by claim 17 wherein implanting comprises bilaterally implanting at least the flexible therapy array in the epidural space both medially and laterally adjacent to at least one pedicle.

25. The method as defined by claim 17 further comprising implanting a second flexible therapy array in the epidural space adjacent to at least one pedicle with stimulation contacts adjacent to one or both of the dorsal column and the dorsal root entry zone of a second dorsal root, the flexible therapy array also being within the normal vertebral foramen, the second flexible therapy array having a substrate configured to be conformable to the dura mater after said implanting.

26. The method as defined by claim 17 wherein the plurality of pedicles includes a right pedicle and a left pedicle, the flexible therapy array spanning substantially from at least the left pedicle to at least the right pedicle within the epidural space after said implanting.

27. The method as defined by claim 17 wherein the plurality of stimulation contacts forms an array of stimulation contacts, the array having at least four rows and at least four columns, the array having no more than 20 rows and 20 columns.

28. The method as defined by claim 17 wherein the prescribed thickness of at least one region of the substrate is between about 0.1 mm and about 1.0 mm.

29. The method as defined by claim 17 wherein the substrate is configured to be curved on at least two intersecting planes.

30. The method as defined by claim 17 wherein the person has cerebrospinal fluid, further wherein medically uncompressed implantation is configured not to compress the dura mater and/or cerebrospinal fluid more than 1.2 mm after said implanting to mitigate abnormal dorsal root activation.

31. A method of assisting a person having spinal cord neural tissue including a plurality of ascending dorsal column fibers and dorsal roots protected by a dura mater and cerebrospinal fluid, the surrounding tissue forming an epidural space, the person also having at least two pedicles and a vertebral foramen, the method comprising:
providing an electrode array having a substrate supporting at least one continuous conductive element defined by a stimulation contact, a wire-receiving contact, and an interconnect between the stimulation contact and the wire-receiving contact, the continuous conductive element formed such that there are no joints connecting (1) the interconnect to the wire-receiving proximal contact, and (2) the interconnect to the stimulation contact,
the stimulation contact configured to stimulate at least a portion of the spinal cord neural tissue, the substrate having a thickness of between 0.1 mm and 1.5 mm, and the continuous conductive element having a thickness of between 10 um and 150 um; and
implanting, in a medically uncompressed manner, the electrode array in the epidural space where a portion of the electrode array is positioned adjacent to at least one pedicle with a stimulation contact adjacent to at least one dorsal root and/or rootlet laterally and/or at least one fasciculi of the dorsal column within the vertebral foramen at one or more vertebral levels.

32. The method as defined by claim 31 wherein the vertebral foramen comprises a normal vertebral foramen.

33. The method as defined by claim 31 wherein implanting comprises implanting the array so that at least one of the stimulation contacts is adjacent to at least one of the dorsal column fibers.

34. The method as defined by claim 31 wherein each dorsal root has a dorsal root entry zone, wherein implanting comprises implanting the flexible array so that at least one of the stimulation contacts is adjacent to at least one of the dorsal root entry zones.

35. The method as defined by claim 31 further comprising actuating the electrode array after said implanting to stimulate at least one portion of the dorsal column fibers.

* * * * *